US006784161B2

(12) United States Patent
Ismaili et al.

(10) Patent No.: US 6,784,161 B2
(45) Date of Patent: Aug. 31, 2004

(54) METHOD FOR THE TREATMENT OR PREVENTION OF FLAVIVIRUS INFECTIONS USING NUCLEOSIDE ANALOGUES

(75) Inventors: Hicham Moulay Alaoui Ismaili, Montreal (CA); Yun-Xing Cheng, Dollard-des-Ormeaux (CA); Jean-François Lavallée, Bellefeuille (CA); Arshad Siddiqui, Dollard-des-Ormeaux (CA); Richard Storer, Baie d'Urfé (CA)

(73) Assignee: BioChem Pharma, Inc., Laval (CA)

( * ) Notice: Subject to any disclaimer, the term of this patent is extended or adjusted under 35 U.S.C. 154(b) by 0 days.

(21) Appl. No.: 09/785,235

(22) Filed: Feb. 20, 2001

(65) Prior Publication Data

US 2002/0019363 A1 Feb. 14, 2002

Related U.S. Application Data
(60) Provisional application No. 60/183,349, filed on Feb. 18, 2000.

(51) Int. Cl.$^7$ ............... A01N 43/04; A61K 31/70
(52) U.S. Cl. ............... 514/43; 514/45; 514/46; 514/47; 514/48; 514/49; 514/50; 514/51; 536/28.1; 536/28.2; 536/28.3; 536/28.4; 536/28.6; 548/952
(58) Field of Search ............... 514/43, 45, 46, 514/47, 48, 49, 50, 51; 536/28.1, 28.2, 28.3, 28.4, 28.6; 548/952

(56) References Cited

U.S. PATENT DOCUMENTS

| 4,963,662 A | * | 10/1990 | Matthes et al. ............... 536/23 |
| 5,506,215 A | * | 4/1996 | Johansson et al. ............ 514/50 |
| 5,705,522 A | * | 1/1998 | Hamedi-Sangsari et al. ............... 514/423 |
| 6,110,901 A | | 8/2000 | Gluzman |

FOREIGN PATENT DOCUMENTS

| EP | 0322384 | 3/1996 | |
| EP | 1046648 | 10/2000 | |
| WO | WO 94/26761 | 11/1994 | |
| WO | WO 98/18324 | 5/1998 | |
| WO | WO 99/43691 | 9/1999 | |
| WO | WO 00/50064 | * 8/2000 | .......... A61K/38/21 |
| WO | WO 00/62799 | 10/2000 | |
| WO | WO 02/18404 | 3/2002 | |

OTHER PUBLICATIONS

Mikhailopulo et al. J. Med. Chem. (1991), vol. 34, pp. 2195–2202.*
Brillanti et al. Ital. J. Gastroenterol Hepatol (1999), vol. 31, pp. 130–134.*

Tai Shun et al., Synthesis and Anticancer Activity of Various 3'–Deoxy Pyrimidine Nucleoside Analogues and Crystal Structure of 1–(3–Deoxy–b–D–threo–pentofuranosyl) cytosine.

Mineo Saneyoshi et al., Synthetic Nucleosides and Nucleotides. XXXV. Synthesis and Biological Evaluations of 5–Fluoropyrimidine Nucleosides and Nucleotides of 3–Deoxy–β–D–ribofuranose and Related Compounds.

Janos Ludwig and Fritz Eckstein, "Rapid and Efficient Synthesis of Nucleoside 5'–O–(1–Thiotriphosphates), 5'–Triphosphates and 2',3'–Cyclophosphorothioates Using 2–Chloro–4H–1,3,2–benzodioxaphosphorin–4–one", J. Org. Chem. 1989, 54, 631–635.

Stephen Hanessian and Pierre Lavellée, "The Preparation and Synthetic Utility of tert–Butyldiphenylsilyl Ethers", Can. J. Chem. 1975, 53(19), 2975–2977.

Stephen H. Kawai et al., "Synthesis of Branched–China And Bicyclic Thiosugar Nucleosides" from Nucleosides Nucleotides, edited by Leroy B. Towsend, 1988 Plenum Press Volumes 1 and 2, 1990, 9(8), 1045–1060.

Krzystof W. Pankiewicz et al., J. Org. Chem. 1992, 57, 7315–7321, Synthesis of 2'–β–Fluoro–and 3'–α–Fluoro–Substituted Guanine Nucleosides. Effects of Sugar Conformational Shifts on Nucleophilic Displacement of the 2'–Hydroxy and 3'–Hydroxy Group with DAST.

Igor A. Mikhailopulo et al., J. Med. Chem. 1991, 34, 2195–2202, Synthesis and Antiviral and Cytostatic Properties of 3'–Deoxy–3'–Deoxy–3'–fluoro–and 2'–Azido–3'–fluoro–2',3'–dideoxy–D–ribofuranosides of Natural Heterocyclic Bases.

Frédéric Puesch et al., Chem. Commun. 1989, (14), 955–957, Synthesis of 9–(3–Deoxy–3–fluoro–β–D–ribofuranosylguanine, a New Potent Antiviral Agent.

Van Aerschot et al., Antiviral Research, 12, 1989, 133–150, Synthesis and Antiviral Activity Evaluation of 3'–fluoro–3'–deoxyribonucleosides: Broad–Spectrum Antiviral Activity of 3'–fluoro–3'–deoxyadenosine.

Igor A. Mikhailopulo et al., FEBS Lett. 1989, 250(2), 139–141, 3'–Fluoro–3'–deoxyribonucleoside 5'–triphosphates: Synthesis and Use as Terminators of RNA Biosynthesis.

Hemant K. Misra et al., J. Heterocycl. Chem., May–Jun. 1984; 21(3), 773–775, Reaction of 1–(2,–3'–Epoxy–β–D–lyxofuranosyl)uracil with Hydrogen Fluoride. The Unexpected Formation of 1–(3'–Fluoro–3'–deoxy–β–ribofuranosyluracil.

(List continued on next page.)

Primary Examiner—Patrick T Lewis
(74) Attorney, Agent, or Firm—Millen, White, Zelano & Branigan

(57) ABSTRACT

The present invention relates to a method for the treatment or prevention of Flavivirus infections using nucleoside analogues in a host comprising administering a therapeutically effective amount of a compound having the formula I or a pharmaceutically acceptable salt thereof.

38 Claims, No Drawings

OTHER PUBLICATIONS

G. Kowollik et al., J. Carbohydr. Nucleosides, Nucleotides, 1975, 2(3), 191–195, Nucleosides of Fluorocarbohydrates, XIII Synthesis of 3'-deoxy'3'-fluorouridine.

Tokumi Maruyama et al., Nucleic Acids Symp. Ser. 1997, 37, 17–18, Synthesis of the 2'-deoxy-2'-fluoro and 3'-deoxy-3'fluoro analogues of B-nromoadenosine.

Tokumi Maruyama et al., Nucleosides & Nucleotides 1998, 17(1–3), 115–122, Synthesis of 8-substituted Analogus of 3'-deoxy-3'-fluoradenosine.

Giordani et al., Nucleosides & Nucleotides 1991, 10(1–3), 719–721, A New Synthesis of 3'-Fluoro-3'-deoxyadenosine.

Carlo Battistini et al., Synthesis, 1990, (10), 900–905, Synthesis of 3'-Fluoro-3'-deoxyadenosine Starting from Adenosine.

Andrea Neumann et al., Z. Chem., 1989, 29(6), 209–210, Uber die Synthese von 3'-desoxy-3'-fluoradenosin dureh chemische Transglykosidierlung.

Yoshitomi Morizawa et al., Bull. Chem. Soc. Jpn., Jun. 1989, 62(6), 2119–2120, Stereoselective Synthesis of 3'-Deoxy-3'-fluoradenosine.

P. Herdewijn et al., Nucleosides & Nucleotides, 1989, 8(1), 65–96, Synthesis of Nucleosides Fluorinated in the Sugar Moiety. The Application of Diethylaminosulfur Trifluoride to the Synthesis of Fluorinated Nucleosides.

Elzbieta Lewandowska et al., Tetrahedron, 1997, 53(18), 6295–6302, Efficient Removal of Sugar A–Tosyl Groups and Heterocycle Halogens from Purine Nucleosides with Sodium Haphthalenide.

P. Herdewijn et al., J. Med. Chem., 1987, 30(11), 2131–2137, P. Herdewijn et al., Synthesis and Anti–HIV Activity of Various 2'-and 3'-Substituted 2',3'-Dedeoxyadenosines: A Structure–activity Analysis.

V.I. Koblinskaya et al., Bioorg. Khim., 1994, 20(11), 1226–1230, Synthesis of Fluoro and Aido Derivatives of Purine Nucleosides from Nucleosides 2',3'-Cyclosulphates.

Piet Herdewijn et al., Helvetica Chim. Acta, 1991, 74(1), 7–23, Synthesis of Modified Oligomeric 2'–5' A Analogues: Potential Antiviral Agents.

Hiroyuki Hayakawa et al., Chem. Pharm. Bull., 1990, 38(5), 1136–1139, Diethylaminosulfur (DAST) as a Fluorinating Agent of Pyrimidine Nucleosides Having a 2',3'-Vicinal Diol System.

Frédéric Puech et al., Tetrahedron Lett., 1990, 30(24), 3171–3174, Synthesis of 9–(3–Deoxy–and 2,3–Dideoxy–3–Fluoro–β–D–Xylofuranoysyl) Guanines as Potential Antiviral Agents.

Morris J. Robins et al., J. Org. Chem., 1974, 39(11), 1564–1570, Nucleic Acid Related Compounds, 11.Adenosine 2',3'–ribo–Expoxide. Synthesis, Intramolecular Degradation, and Transformation into 3'–Substituted Xylofuranosyl Nucleosoides and the lyxo–Epoxidel.

John A. Wright et al., J. Med. Chem., 1970, 13(2), 269–272, Nucleosides. LXIV. Fluoro Sugar Analogs of Arabinosyl– and Xylosyletosines.

J.A. Wright et al., Carbohyd. Res., 1968, 6(3), 347–54, Fluorocarbohydrates Part XVIII. 9–(3–Deoxy–3–Fluoro–β–D–Xylofuranosyl) Adenine and 9–(3–Deoxy–3–Fluoro–a–D–Arabinofuranoysyl) Adenine.

Donald E. Bergstrom et al., J. Med. Chem., 1992, 35(18), 3369–3372, 3',3'-Difluoro-3'-deoxythymidine: Comparison of Anti–HIV Activity to 3'–Fluoro–3'–deoxythymidine.

Vincente Samano et al., Tetrahedron Lett., 1994, 35(21), 3445–3448, Synthesis of 3'-Deoxyadenosine-3'Spirocyclopropane, 3'–Deoxy–Uridine–3'–Spirocyclopropane, and 5'-Deoxy-4',5'-Methanoadenosine.

Panagiotis Ioannidis et al., Nucleosides & Nucleotides, 1993, 12(8), 865–877, Synthesis of 2',3'–Didehydro–2', 3'-Dideoxy-3'-C-Methyl Substituted Nucleosides.

Vincente Samano et al., Can. J. Chem., 1993, 71(2), 1868–191, Nucleic Acid Related Compounds. 77. 2',3'-Didehydro-2',3'-dideoxy-2'(and 3')-methylnucleosides via [3,3]-sigmatropic rearrangements of 2'(and 3')-methylene-3'(and 2')-O-thiocarbonyl derivatives and radical reduction of a 2'-chloro-3'-methylene analogue.

Morris J. Robins et al., J. Med. Chem., 1992, 35(12), 2283–2293, Nucleic Acid Related Compounds. 74. Synthesis and Biological Activity of 2'(and 3')–Deoxy–2'(and 3')–methylenenucleoside Analogues that Function as Mechanism–Based Inhibitors of S–Adenoyl–L–homocysteine Hydrolase and/or Ribonucleotide Reductase.

Tai–shun Lin et al., J. Med. Chem., 1991, 34(8), 2607–2615, Synthesis and Anticancer and Antiviral Activities of Various 2'– and 3'–Methylidene–Substituted Nucleoside Analogues and Crystal Structure of 2'–Deoxy–2'–methylidenecytidine Hydrochloride.

Vincente Samano et al., Synthesis, 1991, (4), 283–288, Stereoselective Addition of a Wittig Reagent To Give a Single Nucleoside Oxaphosphetane Diastereoisomer, Synthesis of 2'(and 3')–methyleneuridine (and cytidine) Derivatives from Uridine Ketonucleosides.

Jean M.J. Trochet et al., Helvetica, Chim. Acta. 1981, 64(2), 425–429, 42. Un nouvel exemple de nucléoside à sucre ramifié insaturé: la désoxy–3'–méthylidé–3'–adénosine.

Vincente Samano et al., J. Org. Chem., 1991, 56(25), 7108–7113, Nucleic Acid Related Compounds. 70. Synthesis of 2'(and 3')–Deoxy–2' (and 3')–methyleneadenosines and Bis (methylene)furan 4',5'–Didehydro–5'–deoxy–2'(and 3')–methyleneadenosines. Inhibitors of S–Adenoyl–L–homocysteine Hydrolase and Ribonucleotide Reductase.

Akira Matsuda et al., Nucleosides & Nucleotides, 1992, 11(2–4), 197–226, Nucleosides and Nucleotides. 104. Radical and Palladium–Catalyzed Deoxygenation of the Allylic Alcohol Systems in the Sugar Moiety of Pyrimidine Nucleosides.

Pawel J. Serafinowski et al., Nucleosides & Nucleotides, 1997, 167(7–9), 1529–1532, Synthesis and NMR Spectra of some new Carbohydrate modified Uridine Phosphoramidites.

Pawel J. Serafinowski et al., Tetrahedron, 1996, 52 (23), 7929–7938, New Method for the Preparation of 3'–and 2'-Phosphoramidites of 2'– and 3'-Difluoromethyleneuridine.

Sven–Erik Behrens et al., EMBO 15, 1996, 12–22, Identification and Properties of the RNA–dependent RNA Polymerase of Hepatitis C Virus.

Volker Lohmann et al., J. Virol., 1997, 71, 8416–8428, Biochemical Properties of Hepatitis C Virus NS5B RNA–Dependent RNA Polymerase and Identification of Amino Acid Sequence Motifs Essential for Enzymatic Activity.

Vladimir D. Axelrod et al., Biochemistry, 1995, 24, 5716–5723, Transcription from Bacteriophase T7 and SP6 RNA Polymerase Promoters in the Presence of 3'=Deoxyribonucleoside 5'–Triphosphate Chain Terminators.

Vladimir D. Axelrod et al., Nucleic Acids Research, vol. 5, No. 10, Oct. 1978, 3549–3563, Specific termination of RNA Polymerase Synthesis as a method of RNA and DNA sequencing.

Gilles Gosselin et al., J. Med. Chem., 1986, 29, 203–213, Systematic Synthesis and Biological Evaluation of α–and β–D–Zylofuranoysl Nucleosides of the Five Naturally Occurring Bases in Nucleic Acids and Related Analogues.

Satoru Suzuki et al., Molecular Pharmacology, 30, 301–306, A Proposed Mechanism for the Selective Inhibition of Human Cytomegalovirus Replication by 1–(2'–Deoxy–2'–fluoro–β–D–Arabinofuranosyl)–5–fluorouracil.

J.M. Crance et al., Journal of Medical Virology 31, 1990, 155–160, Inhibition of Hepatitis A Virus Replication in Vitro by Antiviral Compounds.

Minzo Saneyoshi et al., Chem. Pharm. Bulletin, 30, (6), 1982, 2223–2227, Synthetic Nucleosides and Nucleotides. XIX. Synthesis of 3'–Deoxycytidine 5'–Triphosphate and Related 3'–Deoxy–ribonucleotides from Cordycepin.

Biswendu b. Goswami et al., Journal of Virology, Mar. 1983, vol. 45, No. 3, 1164–1167, Inhibition of Vaccinia Virus Growth and Virus–Specific RNA Synthesis by 3'–O–Methyl Adenosine and 3'–O–Methyl Guanosine.

Rutschmann et al., "Impact of Treatment with Human Immunodeficiency Virus (HIV) Protease Inhibitors on Hepatitis C Viremia in Patients Coinfected with HIV", *The Journal of Infectious Diseases,* 1998, pp783–185, vol. 177.

Ahmed et al., "Treatment Strategies for Chronic Hepatitic C: Update Since the 1997 National Institutes of Health Consensus Development Conference", Journal of Gastroenterology and Hepatology, 1999, pp S12–S18, vol. 14.

Brillanti et al., "Pilot Study of Triple Antiviral Therapy for Chronic Hepatitic C in Interferon Alpha Non–responders", *Ital. J. Gastroenterol. Hepatol.* 1999, pp 130–134, Vol 31.

EP International Search Report dated Jun. 10, 2002.

* cited by examiner

METHOD FOR THE TREATMENT OR PREVENTION OF FLAVIVIRUS INFECTIONS USING NUCLEOSIDE ANALOGUES

This application claims the benefit of U.S. provisional application Serial No. 60/183,349, filed Feb. 18, 2000.

FIELD OF THE INVENTION

The present invention relates to a method for the treatment or prevention of Flavivirus infections using nucleoside analogues.

BACKGROUND OF THE INVENTION

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus (HCV).

HCV is a positive-stranded RNA virus belonging to the Flaviviridae family and has closest relationship to the pestiviruses that include hog cholera virus and bovine viral diarrhea virus (BVDV). HCV is believed to replicate through the production of a complementary negative-strand RNA template. Due to the lack of an efficient culture replication system for the virus, HCV particles were isolated from pooled human plasma and shown, by electron microscopy, to have a diameter of about 50–60 nm. The HCV genome is a single-stranded, positive-sense RNA of about 9,600 bp coding for a polyprotein of 3009–3030 amino-acids, which is cleaved co- and post-translationally by cellular and two viral proteinases into mature viral proteins (core, E1, E2, p7, NS2, NS3, NS4A, NS4B, NS5A, NS5B). It is believed that the structural proteins, E1 and E2, the major glycoproteins are embedded into a viral lipid envelop and form stable heterodimers. It is also believed that the structural core protein interacts with the viral RNA genome to form the nucleocapsid. The nonstructural proteins designated NS2 to NS5 include proteins with enzymatic functions involved in virus replication and protein processing including a polymerase, protease and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

The only treatment currently available for HCV infection is interferon-α (IFN-α). However, according to different clinical studies, only 70% of treated patients normalize alanine aminotransferase (ALT) levels in the serum and after discontinuation of IFN, 35% to 45% of these responders relapse. In general, only 20% to 25% of patients have long-term responses to IFN. Clinical studies have shown that combination treatment with IFN and ribavirin (RIBA) results in a superior clinical response than IFN alone. Different 30 genotypes of HCV respond differently to IFN therapy, genotype 1b is more resistant to IFN therapy than type 2 and 3.

There is therefore a great need for the further development of anti-viral agents.

SUMMARY OF THE INVENTION

The present invention relates to a method for the treatment or prevention of Flavivirus infections in a host comprising administering a therapeutically effective amount of a compound having the formula I or a pharmaceutically acceptable salt thereof:

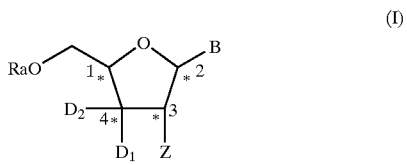

(I)

wherein
B is chosen from a purine, a pyrimidine or an analogue thereof;
Ra is chosen from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

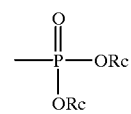

wherein each Rc are independently chosen from H, $C_{1-6}$ alkyl, $C_{2-6}$ alkenyl, $C_{2-6}$ alkynyl, $C_{6-10}$ aryl and an hydroxy protecting group; and
Z is halogen or ORb, wherein Rb is chosen from of H, $C_{1-6}$ alkyl, $C_{2-6}$ alkenyl, $C_{2-6}$ alkynyl, $C_{1-6}$ acyl, or an hydroxy protecting group
$D_1$ and $D_2$ are independently selected from $N_3$, F, or H , $D_1$ and $D_2$ can also be joined to be chosen from $C_3$-cycloalkyl, —=$CH_2$, or —=$CF_2$, and
wherein said compound is in the form of a single enantiomer or a mixture thereof including racemic mixtures;
with the proviso that when B is adenine, Z is ORb, $D_1$ is H, $D_2$ is H and Rb is H, Ra is not triphosphate or H.

In another aspect, there is provided a pharmaceutical formulation comprising the compounds of the invention in combination with a pharmaceutically acceptable carrier or excipient.

Still another aspect, there is provided a method for treating or preventing a viral infection in a host comprising administering a combination comprising at least one compound according to formula I and at least one further therapeutic agent.

In another aspect of the invention is the use of a compound according to formula I, for the preparation of a medicament for treating or preventing a viral infections in a host.

DETAILED DESCRIPTION OF THE INVENTION

In one embodiment, the viral infection is chosen from Flavivirus infections.

In one embodiment, the Flavivirus infection is chosen from Hepatitis C virus (HCV), bovine viral diarrhea virus (BVDV), hog cholera virus and yellow fever virus.

In an other embodiment, the Flavivirus infection is Hepatitis C virus.

In one embodiment, there is also provided a method for inhibiting or reducing the activity of viral polymerase in a host comprising administering a therapeutically effective amount of a compound having the formula I.

In another embodiment, the viral polymerase is HCV polymerase.

The present invention relates to a method for the treatment or prevention of Flavivirus infections using nucleoside analogues in a host comprising administering a therapeutically effective amount of a compound having the formula Ia or a pharmaceutically acceptable salt thereof:

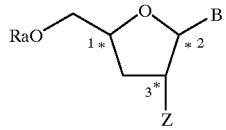

(Ia)

wherein
B is chosen from a purine, a pyrimidine or an analogue thereof;
Ra is chosen from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

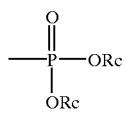

wherein each Rc are independently chosen from H, $C_{1-6}$ alkyl, $C_{2-6}$ alkenyl, $C_{2-6}$ alkynyl, $C_{6-10}$ aryl and an hydroxy protecting group; and
Z is halogen or ORb, wherein Rb is chosen from of H, $C_{1-6}$ alkyl, $C_{2-6}$ alkenyl, $C_{2-6}$ alkynyl, $C_{1-6}$ acyl, or an hydroxy protecting group; and
wherein said compound is in the form of a single enantiomer or a mixture thereof including racemic mixtures;
with the proviso that when B is adenine, Z is ORb and Rb is H, Ra is not triphosphate or H.

In one embodiment, the compounds and methods of the present invention comprise those wherein the following embodiments are present, either independently or in combination.

In one embodiment, B is chosen from adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, uracil-1-yl, 3-carboxamido-1,2,4-triazol-1-yl, 1-deaza-adenin-9-yl, 1-deaza-guanin-9-yl, 1-deaza-inosin-9-yl, 1-deaza-2-amino-purin-9-yl, 1-deaza-2-amino-6-chloro-purin-9-yl, 1-deaza-2-6-diamino-purin-9-yl, 3-deaza-adenin-9-yl, 3-deaza-guanin-9-yl, 3-deaza-inosin-9-yl, 3-deaza-2-amino-purin-9-yl, 3-deaza-2-amino-6-chloro-purin-9-yl 3-deaza-2-6-diamino-purin-9-yl, 7-deaza-adenin-9-yl, 7-deaza-guanin-9-yl, 7-deaza-inosin-9-yl, 7-deaza-2-amino-purin-9-yl, 7-deaza-2-amino-6-chloro-purin-9-yl, 7-deaza-2-6-diamino-purin-9-yl, 7-deaza-8-aza-adenin-9-yl, 7-deaza-8-aza-guanin-9-yl, 7-deaza-8-aza-inosin-9-yl, 7-deaza-8-aza-2-amino-purin-9-yl, 7-deaza-8-aza-2-amino-6-chloro-purin-9-yl, 7-deaza-8-aza-2-6-diamino-purin-9-yl, 8-aza-adenin-9-yl, 8-aza-guanin-9-yl, 8-aza-inosin-9-yl, 8-aza-2-amino-purin-9-yl, 8-aza-2-amino-6-chloro-purin-9-yl, 8-aza-2-6-diamino-purin-9-yl, 2-aza-adenin-9-yl, 2-aza-guanin-9-yl, 2-aza-inosin-9-yl, 2-aza-2-amino-purin-9-yl, 2-aza-2-amino-6-chloro-purin-9-yl, 2-aza-2-6-diamino-purin-9-yl, 3-deaza-thymin-1-yl, 3-deaza-cytosin-1-yl, 3-deaza-uracil-1-yl, 5-aza-thymin-1-yl, 5-aza-cytosin-1-yl, 5-aza-uracil-1-yl, 6-aza-thymin-1-yl, 6-aza-cytosin-1-yl, 6-aza-uracil-1-yl each of which is unsubstituted or substituted by at least one of $NHR_3$, $C_{1-6}$alkyl, $—OC_{1-6}$alkyl, Br, Cl, F, I or OH, wherein $R_3$ is H, $C_{1-6}$alkyl or $C_{1-6}$acyl.

In one embodiment, B is chosen from adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, uracil-1-yl, 3-carboxamido-1,2,4-triazol-1-yl, 3-deaza-adenin-9-yl, 3-deaza-guanin-9-yl, 3-deaza-inosin-9-yl, 3-deaza-2-amino-purin-9-yl, 3-deaza-2-amino-6-chloro-purin-9-yl 3-deaza-2-6-diamino-purin-9-yl, 7-deaza-adenin-9-yl, 7-deaza-guanin-9-yl, 7-deaza-inosin-9-yl, 7-deaza-2-amino-purin-9-yl, 7-deaza-2-amino-6-chloro-purin-9-yl, 7-deaza-2-6-diamino-purin-9-yl, 7-deaza-8-aza-adenin-9-yl, 7-deaza-8-aza-guanin-9-yl, 7-deaza-8-aza-inosin-9-yl, 7-deaza-8-aza-2-amino-purin-9-yl, 7-deaza-8-aza-2-amino-6-chloro-purin-9-yl, 7-deaza-8-aza-2-6-diamino-purin-9-yl, 8-aza-adenin-9-yl, 8-aza-guanin-9-yl, 8-aza-inosin-9-yl, 8-aza-2-amino-purin-9-yl, 8-aza-2-amino-6-chloro-purin-9-yl, 8-aza-2-6-diamino-purin-9-yl, 2-aza-adenin-9-yl, 2-aza-guanin-9-yl, 2-aza-inosin-9-yl, 2-aza-2-amino-purin-9-yl, 2-aza-2-amino-6-chloro-purin-9-yl, 2-aza-2-6-diamino-purin-9-yl, 3-deaza-thymin-1-yl, 3-deaza-cytosin-1-yl, 3-deaza-uracil-1-yl, 5-aza-thymin-1-yl, 5-aza-cytosin-1-yl, 5-aza-uracil-1-yl, 6-aza-thymin-1-yl, 6-aza-cytosin-1-yl, 6-aza-uracil-1-yl each of which is unsubstituted or substituted by at least one of $NHR_3$, $C_{1-6}$alkyl, $—OC_{1-6}$alkyl, Br, Cl, F, I or OH, wherein $R_3$ is H, $C_{1-6}$alkyl or $C_{1-6}$acyl.

In one embodiment, B is chosen from adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, uracil-1-yl, 3-carboxamido-1,2,4-triazol-1-yl, 3-deaza-adenin-9-yl, 3-deaza-guanin-9-yl, 3-deaza-inosin-9-yl, 3-deaza-2-amino-purin-9-yl, 3-deaza-2-amino-6-chloro-purin-9-yl 3-deaza-2-6-diamino-purin-9-yl, 7-deaza-adenin-9-yl, 7-deaza-guanin-9-yl, 7-deaza-inosin-9-yl, 7-deaza-2-amino-purin-9-yl, 7-deaza-2-amino-6-chloro-purin-9-yl, 7-deaza-2-6-diamino-purin-9-yl, 7-deaza-8-aza-adenin-9-yl, 7-deaza-8-aza-guanin-9-yl, 7-deaza-8-aza-inosin-9-yl, 7-deaza-8-aza-2-amino-purin-9-yl, 7-deaza-8-aza-2-amino-6-chloro-purin-9-yl, 7-deaza-8-aza-2-6-diamino-purin-9-yl, 8-aza-adenin-9-yl, 8-aza-guanin-9-yl, 8-aza-inosin-9-yl, 8-aza-2-amino-purin-9-yl, 8-aza-2-amino-6-chloro-purin-9-yl, 8-aza-2-6-diamino-purin-9-yl, 5-aza-thymin-1-yl, 5-aza-cytosin-1-yl, 5-aza-uracil-1-yl, 6-aza-thymin-1-yl, 6-aza-cytosin-1-yl, 6-aza-uracil-1-yl each of which is unsubstituted or substituted by at least one of $NHR_3$, $C_{1-6}$alkyl, $—OC_{1-6}$alkyl, Br, Cl, F, I or OH, wherein $R_3$ is H, $C_{1-6}$alkyl or $C_{1-6}$acyl.

In one embodiment, B is chosen from adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, uracil-1-yl, 3-carboxamido-1,2,4-triazol-1-yl each of which is unsubstituted or substituted by at least one of $NHR_3$, $C_{1-6}$alkyl, $—OC_{1-6}$alkyl, Br, Cl, F, I or OH, wherein $R_3$ is H, Cl $_6$alkyl or $C_{1-6}$acyl.

In a further embodiment, B is chosen from adenin-9-yl, guanin-9-yl, 2-amino-purin-9-yl, 2-amino-6-chloro-purin-9-yl, 2-6-diamino-purin-9-yl, thymin-1-yl, cytosin-1-yl, uracil-1-yl, each of which is unsubstituted or substituted by at least one of $NHR_3$, $C_{1-6}$alkyl, $—OC_{1-6}$alkyl, Br, Cl, F, I or OH, wherein $R_3$ is H, $C_{1-6}$alkyl or $C_{1-6}$acyl.

In a further embodiment, B is chosen from guanin-9-yl, cytosin-1-yl, uracil-1-yl, each of which is unsubstituted or substituted by at least one of $NHR_3$, $C_{1-6}$alkyl, $—OC_{1-6}$alkyl, Br, Cl, F, I or OH, wherein $R_3$ is H, $C_{1-6}$alkyl or $C_{1-6}$acyl.

In a further embodiment, B is cytosin-1-yl, which is unsubstituted or substituted by at least one of $NHR_3$, $C_{1-6}$alkyl, Br, Cl, F, I or OH, wherein $R_3$ is H, $C_{1-6}$alkyl or $C_{1-6}$acyl.

In a further embodiment, B is guanin-9-yl, which is unsubstituted or substituted by at least one of $NHR_3$, $C_{1-6}$alkyl, Br, Cl, F, I or OH, wherein $R_3$ is H, $C_{1-6}$alkyl or $C_{1-6}$acyl.

In a further embodiment, B is uracil-1-yl, which is unsubstituted or substituted by at least one of $NHR_3$, $C_{1-6}$alkyl, Br, Cl, F, I or OH, wherein $R_3$ is H, $C_{1-6}$alkyl or $C_{1-6}$acyl.

In one embodiment, B is chosen from adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, 5-fluoro-cytosin-1-yl, uracil-1-yl, 5-fluorouracil or 1,2,4-triazole-3-carboxamide base (ribarivin base).

In one embodiment, B is chosen from adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, 5-fluoro-cytosin-1-yl, uracil-1-yl, or 1,2,4-triazole-3-carboxamide base (ribarivin base).

In one embodiment, B is chosen from guanin-9-yl, cytosin-1-yl, 5'-fluoro-cytosin-1-yl, 5'-fluorouracil-1-yl or uracil-1-yl.

In one embodiment, B is chosen from guanin-9-yl, cytosin-1-yl, 5'-fluoro-cytosin-1-yl, 5'-fluorouracil-1-yl or uracil-1-yl.

In one embodiment, B is cytosin-1-yl.
In one embodiment, B is 5-fluoro-cytosin-1-yl.
In one embodiment, B is 5-fluorouracil.
In one embodiment, B is guanin-9-yl.
In one embodiment, B is uracil-1-yl.
In a further embodiment, B is Wherein;
X is H, halogen or $NHR_{10}$, wherein $R_{10}$ is H, $C_{1-6}$acyl, $C_{1-6}$ alkyl, $C_{2-6}$ alkenyl, or $C_{2-6}$ alkynyl;
Y is H, halogen or $NHR_{11}$, wherein $R_{11}$ is H, $C_{1-6}$acyl, $C_{1-6}$ alkyl, $C_{2-6}$ alkenyl, or $C_{2-6}$ alkynyl;
$Y_2$ is H, halogen or $NHR_{12}$, wherein $R_{12}$ is H, $C_{1-6}$acyl, $C_{1-6}$ alkyl, $C_{2-6}$ alkenyl, or $C_{2-6}$ alkynyl;
$R_9$ is H, hydroxy protecting group, $C_{1-6}$acyl, $C_{1-6}$ alkyl, $C_{2-6}$ alkenyl, or $C_{2-6}$ alkynyl;
$Y_3$ is H, halogen or $NHR_{13}$, wherein $R_{13}$ is H, $C_{1-6}$acyl, $C_{1-6}$ alkyl, $C_{2-6}$ alkenyl, or $C_{2-6}$ alkynyl;
$R_7$ is H, halogen, $C_{1-6}$acyl, $C_{1-6}$ alkyl, $C_{2-6}$ alkenyl, or $C_{2-6}$ alkynyl;
$R_8$ is H, halogen, $C_{1-6}$acyl, $C_{1-6}$ alkyl, $C_{2-6}$ alkenyl, or $C_{2-6}$ alkynyl.

In one embodiment,
X is H, halogen or $NHR_{10}$, wherein $R_{10}$ is H.
Y is H, halogen or $NHR_{11}$, wherein $R_{11}$ is H.
$Y_2$ is H, halogen or $NHR_{12}$, wherein $R_{12}$ is H.
$R_9$ is H, hydroxy protecting group, $C_{1-6}$ alkyl.
$Y_3$ is H, halogen or $NHR_{13}$, wherein $R_{13}$ is H.
$R_7$ is H, halogen, or $C_{1-6}$ alkyl.
$R_8$ is H, halogen or $C_{1-6}$ alkyl.

In a further embodiment,
X is H, F, or $NHR_{10}$, wherein $R_{10}$ is H.
Y is H, F, or $NHR_{11}$, wherein $R_{11}$ is H.
$Y_2$ is H, F, or $NHR_{12}$, wherein $R_{12}$ is H.
$R_9$ is H.
$Y_3$ is H, F, or $NHR_{13}$, wherein $R_{13}$ is H.
$R_7$ is H, F, or $C_{1-6}$ alkyl.
$R_8$ is H, F, or $C_{1-6}$ alkyl.

In one embodiment of the invention, Ra is chosen from H, monophosphate, diphosphate, and triphosphate.

In another embodiment of the invention, Ra is H.

In one embodiment, Z is F or ORb, wherein Rb is chosen from of H, $C_{1-6}$ alkyl, $C_{2-6}$ alkenyl, $C_{2-6}$ alkynyl, $C_{1-6}$ acyl, or an hydroxy protecting group.

In one embodiment, Z is F.

In one embodiment, Z is ORb, wherein Rb is chosen from of H, $C_{1-6}$ alkyl, $C_{2-6}$ alkenyl, $C_{2-6}$ alkynyl, $C_{1-6}$ acyl, or an hydroxy protecting group.

In one embodiment, Z is ORb, wherein Rb is chosen from of H, $C_{1-6}$ alkyl, or an hydroxy protecting group.

In one embodiment, Z is ORb, wherein Rb is chosen from of H, or methyl.

In one embodiment, Z is ORb, wherein Rb is H.

$D_1$ and $D_2$ are independently selected from $N_3$, F, or H, $D_1$ and $D_2$ can also be joined to be chosen from cyclopropyl, difluorocyclopropyl ——=$CH_2$, or ——=$CF_2$.

$D_1$ and $D_2$ are independently selected from F, or H, $D_1$ and $D_2$ can also be joined to be chosen from cyclopropyl, difluorocyclopropyl ——=$CH_2$, or ——=$CF_2$.

$D_1$ and $D_2$ are joined and are cyclopropyl.
$D_1$ and $D_2$ are joined and are difluorocyclopropyl.
$D_1$ and $D_2$ are joined and are ——=$CH_2$.
$D_1$ and $D_2$ are joined and are ——=$CF_2$.
In one embodiment, $D_1$ is H or F.
In one embodiment, $D_2$ is H or F.
In one embodiment, $D_1$ is H.
In one embodiment, $D_2$ is H.
In one embodiment, $D_1$ is F.
In one embodiment, $D_2$ is F.
In one embodiment, $D_1$ is $N_3$ and $D_2$ is H.
In one embodiment, $D_1$ is H and $D_2$ is $N_3$.
In one embodiment, $D_1$ is $N_3$ and $D_2$ is F.
In one embodiment, $D_1$ is F and $D_2$ is $N_3$.
In one embodiment, $D_1$ is H and $D_2$ is F.
In one embodiment, $D_1$ is F and $D_2$ is H.
In one embodiment, $D_1$ and $D_2$ are H.
In one embodiment, $D_1$ and $D_2$ are F.

In a further embodiment, the present invention relates to a method for the treatment or prevention of Flavivirus infections using nucleoside analogues in a host comprising administering a therapeutically effective amount of a compound having the formula Ib or a pharmaceutically acceptable salt thereof:

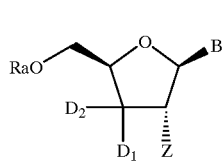

(Ib)

wherein Ra, B, $D_1$, $D_2$ and Z are as defined above.

In a further embodiment, the present invention relates to a method for the treatment or prevention of Flavivirus infections using nucleoside analogues in a host comprising administering a therapeutically effective amount of a compound having the formula Ic or a pharmaceutically acceptable salt thereof:

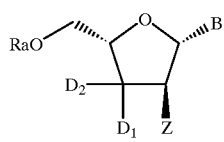

(Ic)

wherein Ra, B, $D_1$, $D_2$ and Z are as defined above.

In a further embodiment, the present invention relates to a method for the treatment or prevention of Flavivirus infections using nucleoside analogues in a host comprising administering a therapeutically effective amount of a compound having the formula Id or a pharmaceutically acceptable salt thereof:

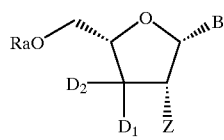

(Id)

wherein Ra, B, $D_1$, $D_2$ and Z are as defined above.

In a further embodiment, the present invention relates to a method for the treatment or prevention of Flavivirus infections using nucleoside analogues in a host comprising administering a therapeutically effective amount of a compound having the formula Ie or a pharmaceutically acceptable salt thereof:

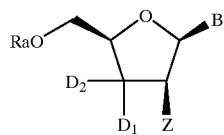

(Ie)

wherein Ra, B, $D_1$, $D_2$ and Z are as defined above.

In a further embodiment, the present invention relates to a method for the treatment or prevention of Flavivirus infections using nucleoside analogues in a host comprising administering a therapeutically effective amount of a compound having the formula If or a pharmaceutically acceptable salt thereof:

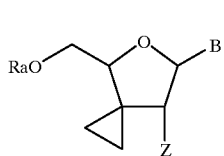

(If)

wherein Ra, B, and Z are as defined above.

In a further embodiment, the present invention relates to a method for the treatment or prevention of Flavivirus infections using nucleoside analogues in a host comprising administering a therapeutically effective amount of a compound having the formula Ig or a pharmaceutically acceptable salt thereof:

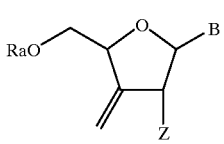

(Ig)

wherein Ra, B, and Z are as defined above.

In a further embodiment, the present invention relates to a method for the treatment or prevention of Flavivirus infections using nucleoside analogues in a host comprising administering a therapeutically effective amount of a compound having the formula Ih or a pharmaceutically acceptable salt thereof:

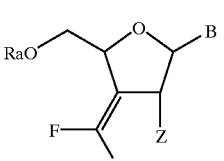

(Ih)

wherein Ra, B, and Z are as defined above.

In a further embodiment, the present invention relates to a method for the treatment or prevention of Flavivirus infections using nucleoside analogues in a host comprising administering a therapeutically effective amount of a compound having the formula Ii or a pharmaceutically acceptable salt thereof:

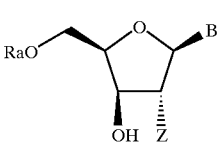

(Ii)

wherein Ra, B, and Z are as defined above.

In one embodiment, a compound of formula (I) is chosen from:

3'-deoxycytidine  
Z = H, Compound #1,  
3'-deoxycytidine-  
5' triphosphate  
Z = triphosphate, Compound #2

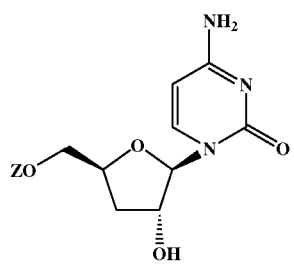

5-Fluoro-3'-deoxycytidine  
Z = H, Compound #3  
5-Fluoro-3'-deoxycytidine-  
5' triphosphate  
Z = triphosphate, Compound #4

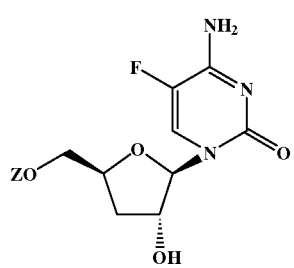

3'-deoxyuridine  
Z = H, Compound #5  
3'-deoxyuridine-  
5' triphosphate  
Z = triphosphate, Compound #6

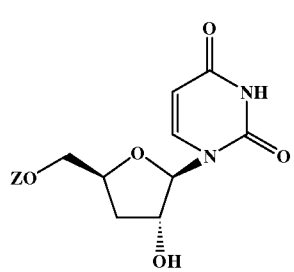

5-Fluoro-3'-deoxyuridine  
Z = H, Compound #7  
5-Fluoro-3'-deoxyuridine-  
5' triphosphate  
Z = triphosphate, Compound #8

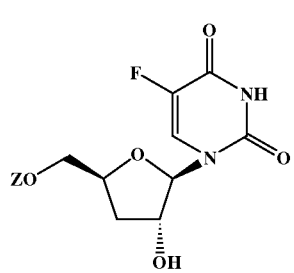

3'-deoxythymidine  
Z = H, Compound #9  
3'-deoxythymidine-  
5' triphosphate  
Z = triphosphate, Compound #10

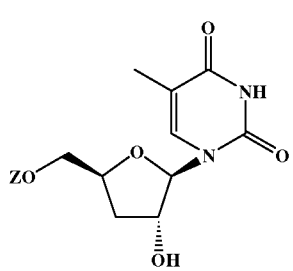

3'-deoxyguanosine  
Z = H,  
Compound #11  
3'-deoxyguanosine-  
5' triphosphate  
Z = triphosphate, Compound #12

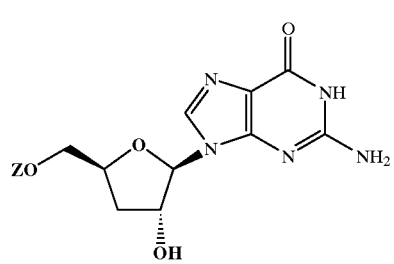

-continued

2-N-acetyl-3'-deoxyguanosine
Z = H, Compound #13
2-N-acetyl-3'-deoxyguanosine-
5' triphosphate
Z = triphosphate, Compound #14

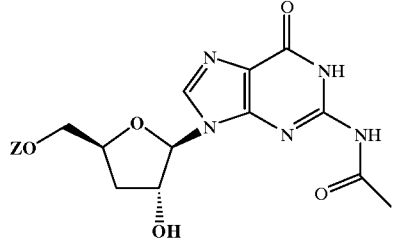

5-Methyl-3'-deoxycytidine
Z = H, Compound #15,
5-Methyl-3'-deoxycytidine-
5' triphosphate
Z = triphosphate, Compound #16

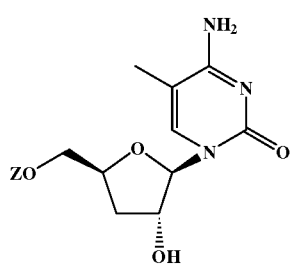

5-Iodo-3'-deoxycytidine
Z = H, Compound #17,
5-Iodo-3'-deoxycytidine-
5' triphosphate
Z = triphosphate, Compound #18

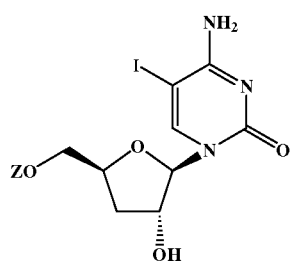

5-Chloro-3'-deoxycytidine
Z = H, Compound #19,
5-=Chloro-3'-deoxycytidine-
5' triphosphate
Z = triphosphate, Compound #20

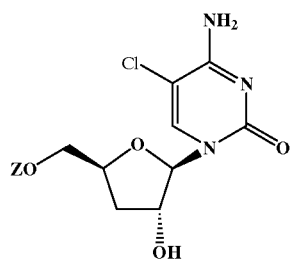

3'-fluoro-3'-deoxyguanosine
Z = H, Compound #21
3'-fluoro-3'-deoxyguanosine -
5' triphosphate
Z = triphosphate, Compound #22

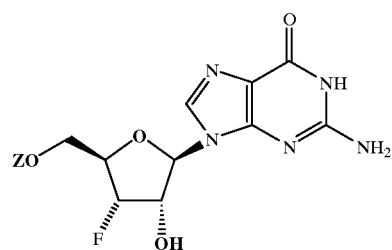

-continued

3'-fluoro 3'-deoxycytidine
Z = H, Compound #23,
3'-fluoro 3'-deoxycytidine-
5' triphosphate
Z = triphosphate, Compound #24

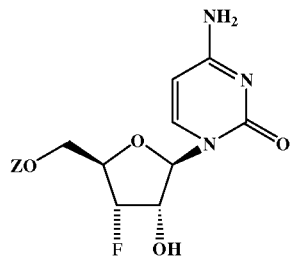

5-Iodo-3'-deoxycytidine
Z = H, Compound #25,
5-=Iodp-3'-deoxycytidine-
5' triphosphate
Z = triphosphate, Compound #26

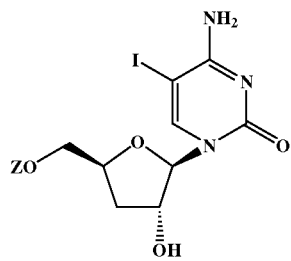

5-Chloro-3'-deoxyuridine
Z = H, Compound #27
5-Chloro -3'-deoxyuridine-
5' triphosphate
Z = triphosphate, Compound #28

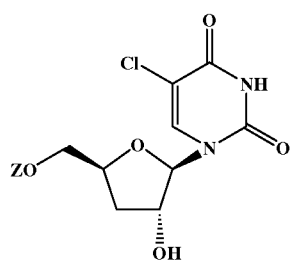

5-Bromo-3'-deoxyuridine
Z = H, Compound #29
5-Bromo -3'-deoxyuridine-
5' triphosphate
Z = triphosphate, Compound #30

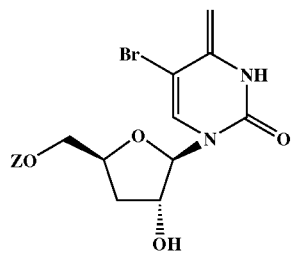

6-Chloro-3'-deoxyguanosine
Z = H, Compound #31
6-Chloro-3'-deoxyguanosine -
5' triphosphate
Z = triphosphate, Compound #32

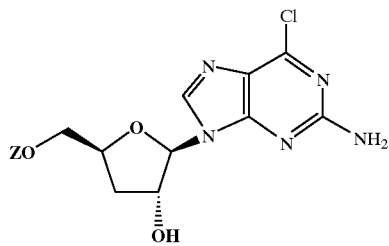

3'-spirocyclopropyl-3'-
deoxyguanosine
Z = H, Compound #33
3'-spirocyclopropyl-3'-
deoxyguanosine
5' triphosphate
Z = triphosphate, Compound #34

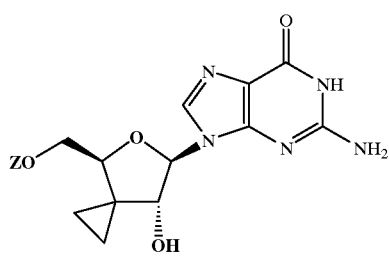

-continued

3'-difluoro-spirocyclopropyl-
3'-deoxyguanosine
Z = H, Compound #35
3'- difluoro-
spirocyclopropyl-3'-
deoxyguanosine
5' triphosphate
Z = triphosphate, Compound #36

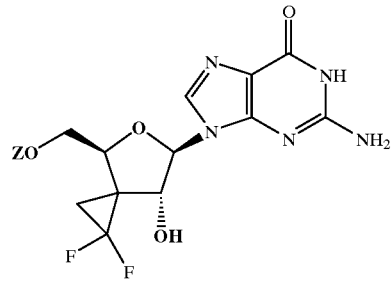

3'-methylene-3'-
deoxyguanosine
Z = H, Compound #37
3'-methylene-3'-
deoxyguanosine -
5' triphosphate
Z = triphosphate, Compound #38

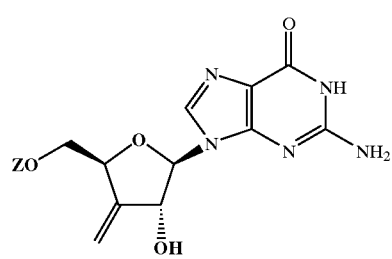

3'-difluromethylene 3'-
deoxyguanosine
Z = H, Compound #39
3'-difluromethylene 3'-
deoxyguanosine -
5' triphosphate
Z = triphosphate, Compound #40

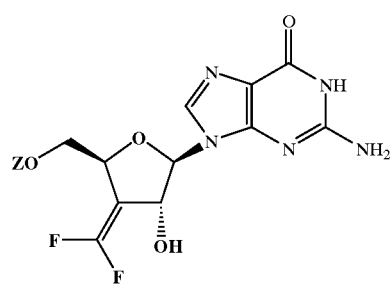

3'-spirocyclopropyl-3'-
deoxycytidine
Z = H, Compound #41
3'-spirocyclopropyl-3'-
deoxycytidine -5' triphosphate
Z = triphosphate, Compound #42

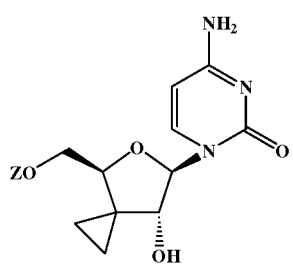

3'-difluoro-spirocyclopropyl
3'- deoxycytidine
Z = H, Compound #43
3'- difluoro-
spirocyclopropyl-3'-
deoxycytidine -5' triphosphate
Z = triphosphate, Compound #44

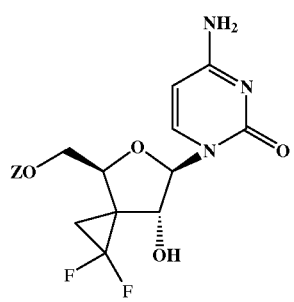

-continued

3'-methylene-3'-deoxycytidine
Z = H, Compound #45
3'-methylene-3'-deoxycytidine -5' triphosphate
Z = triphosphate, Compound #46

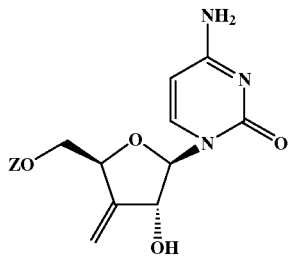

3'-difluromethylene 3'-deoxycytidine
Z = H, Compound #47
3'-difluromethylene 3'-deoxycytidine -5' triphosphate
Z = triphosphate, Compound #48

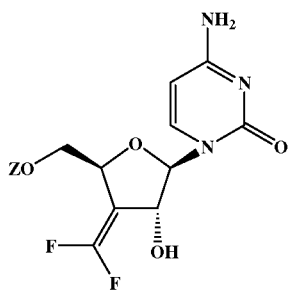

9-β-D-xylofuranosyl-guanosine
Z = H, Compound #49
9-β-D-xylofuranosyl-guanosine -5' triphosphate
Z = 'triphosphate, Compound #50

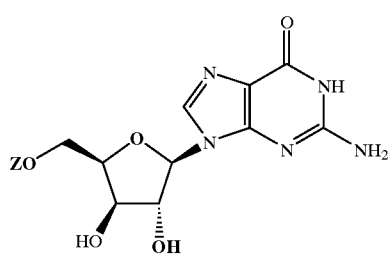

9-β-D-xylofuranosyl-cytidine
Z = H, Compound #51
9-β-D-xylofuranosyl-cytidine -5' triphosphate
Z = triphosphate, Compound #52

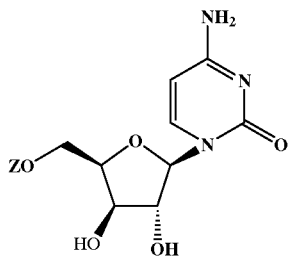

3'-azido-3'-deoxycytidine
Z = H, Compound #53
3'-azido-3'- deoxycytidine 5' triphosphate
Z = triphosphate, Compound #54

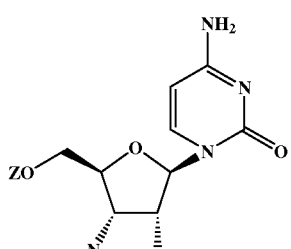

It will be appreciated by those skilled in the art that the compounds of formula (I) contain at least three chiral centres and which are marked by 1, 2 and 3. When D1 and D2 are different, the compounds of formula (I) contain at least four chiral centres which are marked by 1, 2, 3 and 4. The compounds of formula (I) thus exist in the form of different optical isomers (e.g β-L and β-D) and geometric isomers trans or α and cis or β. All such enantiomers, geometric isomers and mixtures thereof including racemic mixtures are included within the scope of the invention. The single optical isomer or enantiomer can be obtained by method well known in the art, such as chiral HPLC, enzymatic resolution and the use of chiral auxiliary.

According to one embodiment, the atoms marked by 1 and 2 are in the cis or β configuration.

According to one embodiment, the atoms marked by 1 and 2 are in the cis or β configuration while the atom marked by 3 is in a trans or α configuration with respect to the atom 1 and 2.

According to one embodiment, compounds of formula I of the present invention are provided substantially in the form of the β-D configuration.

According to one embodiment, compounds of formula I of the present invention are provided substantially in the form of the β-L configuration.

By "substantially" is meant that there is more one enantiomer then of the other enantiomer.

In another embodiment, the compounds of formula I of the present invention are at least 95% free of the corresponding β-D enantiomer.

In another embodiment, the compounds of formula I of the present invention are at least 97% free of the corresponding β-D enantiomer.

Still in another embodiment, the compounds of formula I of the present invention are at least 99% free of the corresponding β-D enantiomer.

In another embodiment, the compounds of formula I of the present invention are at least 95% free of the corresponding β-L enantiomer.

In another embodiment, the compounds of formula I of the present invention are at least 97% free of the corresponding β-L enantiomer.

Still in another embodiment, the compounds of formula I of the present invention are at least 99% free of the corresponding β-L enantiomer.

There is also provided pharmaceutically acceptable salts of the compounds of formula I of the present invention. By the term pharmaceutically acceptable salts of the compounds of formula (I) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids.

Salts derived from appropriate bases include alkali metal (e.g. sodium), alkaline earth metal (e.g. magnesium), ammonium and $NR_4+$ (where R is $C_{1-4}$ alkyl) salts.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in the present application, "compound(s) of formula (I)" refers to all compounds identified by formula (I) and formulae (Ia) to (Ii).

As used in this application, the term "purine or pyrimidine or an analogue thereof" is meant a purine or pyrimidine base found in nucleotide or an analogue thereof which mimics such bases in that their structures (the kinds of atoms and their arrangement) are similar to the normal bases but may possess additional or lack certain of the functional properties of the normal bases. Such analoguses include those derived by replacement of a CH moiety by a nitrogen atom (for example, 5-azapyrimidines such as 5-azacytosine) or vice versa (for example 7-deazapurines, such as 7-deazadenosine or 7-deazaguanosine) or both (e.g. 7-deaza, 8-azapurines).

Analogues of such bases also include those compounds wherein ring substituents are either incorporated, removed or modified by conventional substituents known in the art e.g. halogen, hydroxyl, amino, C1–6 alkyl. Such purine or pyrimidine base, analogues and derivatives will be well known to those skilled in the art.

As used in this application, the term "alkyl" represents an unsubstituted or substituted (by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

As used in this application, the term "cycloalkyl" represents an "alkyl" as defined above which forms a ring.

The terms "alkenyl" and "alkynyl" represent an alkyl containing at least one unsaturated group (e.g. allyl).

The term "hydroxy protecting group" is well known in the field of organic chemistry. Such protecting groups may be found in T. Greene, *Protective Groups In Organic Synthesis*, (John Wiley & Sons, 1981). Example of hydroxy protecting groups include but are not limited to acetyl-2-thioethyl ester, pivaloyloxymethyl ester and isopropyloxycarbonyloxymethyl ester.

The term "aryl" represents an unsaturated carbocyclic moiety, optionally mono- or di-substituted with OH, SH, amino, halogen or $C_{1-6}$ alkyl.

The term "heteroaryl" represents an aryl wherein at least one carbon ring atom is substituted by an heteroatom (e.g. N, O, or S).

The term "aminoalkyl" represents an alkyl which is covalently bonded to the adjacent atom through a nitrogen atom.

The term "thioalkyl" represents an alkyl which is covalently bonded to the adjacent atom through a sulfur atom.

The term "alkoxy" represents an alkyl which is covalently bonded to the adjacent atom through an oxygen atom.

Halogen are chosen from F, Cl, I, and Br.

The term "host" represents any mammals including humans.

In one embodiment, the host is human.

The compounds of the present invention can be prepared by methods well known in the art. For example, such methods are described in the following references *J.Med. .Chem.* 1991, 34; 693–701; *Chem. Pharm. Bull.* 1995, 43(11) 2005–2009; *J.Org.Chem.* 1989, 54, 631–635; *Can. .J.Chem.* 1975, 53(19), 2975–2977; *Nucleosides Nucleotides*, 1990, 9(8), 1045–60 and *Chemistry of Nucleosides and Nucleotides* edited by Leroy B. Towsend, 1988 Plenum Press Volumes 1 and 2; synthesis of 2'-β-fluoro- and 3'-β-fluoro-substituted guanine nucleosides. Effect of sugar conformational shifts on nucleophilic displacement of the 2'-hydroxy and 3'-hydroxy group with DAST. J. Org. Chem., 57(26), (1992) 7315–21. Synthesis and antiviral and cytostatic properties of 3'-deoxy-3'-fluoro- and 2'-azido-3'-fluro-2', 3'-didexy-D-ribofuranosides of natural heterocyclic bases. J. Med. Chem., 34(7), (1991) 2195–2202. Synthesis of 9-(3-deoxy-3-fluoro-β-D-ribofuranosyl) guanine, a new potent antiviral agent. J. Chem. Soc., Chem. Commun. (1989), (14), 955–7. Synthesis and antiviral activity evaluation of 3'-fluoro-3'-deoxyribonucleosides: broad-spectrum antiviral activity of 3'-fluoro-3'-deoxyadenosine. Antiviral Res. (1989), 12(3), 133–50. 3'-Fluoro-3'- deoxyribonucleoside 5'-triphosphates: synthesis and use as terminators of RNA biosynthesis. FEBS Lett. (1989), 250 (2), 139–41. Reaction of 1-(2', 3'epoxy-β-D-lyxofuranosyl) uracil with hydrogen fluoride. The unexpected formation of 1-(3'-fluoro-3'-deoxy-β-D-ribofuranosyl)uracil. J. Heterocycl. Chem. (1984), 21(3), 773–5. Synthesis of 3'-deoxy-3'-fluorouridine. J. Carbohydr., Nucleosides, Nucleotides (1975), 2(3), 191–5. Synthesis of the 2'-deoxy-2'-fluoro and 3'-deoxy-3'-fluoro analogs of 8-bromoadenosine. Nucleic Acids Symp. Ser. (1997), 37 (Symposium on Nucleic Acids Chemistry, 1997), 17–18. Synthesis of 8-substituted analogs of 3'-deoxy-3'-fluoroadenosine. Nucleosides Nucleotides (1998), 17(1–3), 115–122. A new synthesis of 3'-fluoro-3'-deoxyadenosine. Nucleosides Nucleotides (1991), 10(1–3), 719–21. Synthesis of 3'-fluoro-3'-deoxyadenosine starting from adenosine. Synthesis (1990), (10), 900–5. Synthesis of 3'-deoxy-3'-fluoroadenosine by chemical transglycosidation. Z. Chem. (1989), 29(6), 209–10. Stereoselective synthesis of 3'-deoxy-3'-flurroadenosine. Bull. Chem. Soc. Jpn. (1989), 62(6), 2119–20. Synthesis of nucleosides fluorinated in the sugar moiety. The application of diethylaminosulfur trifluoride to the synthesis of fluorinated nucleosides. Nucleosides Nucleotides (1989), 8(1), 65–96. Preparation of difluorouridines as antitumor agents. Efficient removal of sugar O-tosyl groups and heterocycle halogens from purine nucleosides with sodium naphthalenide. Tetrahedron (1997), 53(18), 6295–6302.Synthesis of fluoro and azido derivatives of purine nucleosides from nucleoside 2', 3'-cyclic sulfates. Bioorg. Khim. (1994), 20(11), 1226–30. Synthesis of modified oligomeric 2'–5' A analogs: potential antiviral agents. Helv. Chim. Acta (1991), 74(1), 7–23.Diethylaminosulfur trifluoride (DAST) as a fluorinating agent of pyrimidine nucleosides having a 2',3'-vicinal diol system. Chem. Pharm. Bull. (1990), 38(5), 1136–9. Synthesis of 9-(3-deoxy- and 2,3-dideoxy-3-fluoro-β-D-xylofuranosyl)guanifles as potential antiviral agents. Tetrahedron Lett. (1989), 30(24), 3171–4. Synthesis and anti-HIV activity of various 2'- and 3'-substituted 2', 3'-dideoxyadenosines: a structure-activity analysis. J. Med. Chem. (1987), 30(11), 2131–7. Adenosine 2', 3'-ribo-epoxide. Synthesis, intramolecular degradation, and transformation into 3'-substituted xylofuranosyl nucleosides and the lyxo-epoxide. J. Org. Chem. (1974), 39(11), 1564–70. Fluoro sugar analogs of arabinosyl- and xylosyl-cytosines. J. Med. Chem. (1970), 13(2), 269–72. 9-(3-Dexoxy-3-fluoro-β-D-xylofuranosyl) adenine and 9-(3-deoxy-3-fluro-β-D-arabinofuranosyl) adenine. Carbohyd. Res. (1968), 6(3), 347–54. 3', 3'-Difluoro-3'-deoxythymidine: comparison of anti-HIV activity to 3'-fluoro-3'-deoxythymidine. J. Med. Chem. (1992), 35(18), 3369–72. Nucleic acid related compounds. 83. Synthesis of 3'deoxyadenosine-3'-spirocyclopropane, 3'-deoxyuridine-3'-spirocyclopropane, and 5'-deoxy-4', 5'-methanoadenosine. Tetrahedron Lett. (1994), 35(21), 3445–8. Synthesis of 2', 3'-didehydro-2', 3'-dideoxy-3'-C-methyl substituted nucleosides. Nucleosides Nucleotides (1993), 12(8), 865–77. 2', 3'-Didehydro-2', 3'-dideoxy-2' (and3')-methylnucleosides via [3,3]-sigmatropic rearrangements of 2' (and 3')-methylene-3' (and 2')-O-thiocarbonyl derivatives and radical reduction of a 2'-chloro-3'-methylene analog. Can. J. Chem. (1993), 71(2), 186–91. Synthesis and biological activity of 2' (and 3')-deoxy-2' (and 3')-methylenenucleoside analogs that function as mechanism-based inhibitors of S-adenosyl-L-homocysteine hydrolase and/or ribonucleotide reductase. J. Med. Chem. (1992), 35(12), 2283–93.Synthesis and anticancer and antiviral activities of various 2'- and 3'-methylidene-substituted nucleoside analogs and crystal structure of 2'-deoxy-2'-methylidenecytidine hydrochloride. J. Med. Chem. (1991), 34(8), 2607–15. Stereoselective addition of a Wittig reagent to give a single nucleoside oxaphospetane diastereoisomer. Synthesis of 2' (and 3')-deoxy-2' (and 3')-methyleneuridine (and cytidine) derivatives from uridine ketonucleosides. Synthesis (1991), (4), 282–8. A novel example of unsaturated branched chain sugar nucleoside: 3'-deoxy-3'-methylideneadenosine. Helv. Chim. Acta (1981), 64(2), 425–9. Synthesis of 2' (and 3')-deoxy-2' (and 3')-methyleneadenosines and bis (methylene)furan 4', 5'-didehydro-5'-deoxy-2' (and 3')-methyleneadenosines. Inhibitors of S-adenosyl-L-homocysteine hydrolase and ribonucleotide reductase. J. Org. Chem. (1991), 56(25), 7108–13. Radical and palladium-catalyzed deoxygenation of the allylic alcohol systems in the sugar moiety of pyrimidine nucleosides. Nucleosides Nucleotides (1992), 11(2–4), 197–226. Synthesis and NMR spectra of some new carbohydrate modified uridine phosphoramidites. Nucleosides Nucleotides (1997), 16(7–9), 1529–1532. New method for the preparation of 3'- and 2'-phosphoramidites of 2'- and 3'-difluoromethyleneuridine. Tetrahedron (1996), 52(23), 7929–7938. Nucleic acid related compounds. 83. Synthesis of 3'deoxyadenosine-3'-spirocyclopropane, 3'-deoxyuridine-3'-spirocyclopropane, and 5'-deoxy-4', 5'-methanoadenosine. Some compounds of the present invention are commercially available at Sigma or Aldrich.

According to one embodiment, it will be appreciated that the amount of a compound of formula I of the present invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.01 to about 750 mg/kg of body weight per day, preferably in the range of 0.5 to 60 mg/kg/day, most preferably in the range of 1 to 20 mg/kg/day.

The desired dose according to one embodiment is conveniently presented in a single dose or as divided dose administered at appropriate intervals, for example as two, three, four or more doses per day.

In another embodiment, the compound is conveniently administered in unit dosage form; for example containing 10 to 1500 mg, conveniently 20 to 1000 mg, most conveniently 50 to 700 mg of active ingredient per unit dosage form.

According to another embodiment of the present invention, the active ingredient is administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of formula I of the present invention may be administered as the raw chemical, it is preferable according to one embodiment of the invention, to present the active ingredient as a pharmaceutical formulation. The embodiment of the invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

According to one embodiment of the present invention, pharmaceutical formulations include but are not limited to those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods according to this embodiment include the step of bringing into association the active compound with liquid carriers or finely divided solid carriers or both and then, if necessary, shaping the product into the desired formulation.

According to another embodiment, pharmaceutical formulation suitable for oral administration are conveniently presented as discrete units such as capsules, cachets or tablets each containing a predetermined amount of the active ingredient; as a powder or granules. In another embodiment, the formulation is presented as a solution, a suspension or as an emulsion. Still in another embodiment, the active ingredient is presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of formula I according to an embodiment of the present invention are formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds of formula I, according to one embodiment of the present invention, are formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid. In another embodiment, they are presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

According to one embodiment, the formulations suitable for vaginal administration are presented as pessaries, tampons, creams, gels, pastes, foams or sprays containing in addition to the active ingredient such carriers as are known in the art to be appropriate.

For intra-nasal administration the compounds, in one embodiment of the invention, are used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds, according to one embodiment of the invention are conveniently delivered from an insufflator, nebulizer or a pressurized pack or other convenient means of delivering an aerosol spray. In another embodiment, pressurized packs comprise a suitable propellant such as dichlorodifluoromethane, trichlorofluoromethane, dichlorotetrafluoroethane, carbon dioxide or other suitable gas. In another embodiment, the dosage unit in the pressurized aerosol is determined by providing a valve to deliver a metered amount.

Alternatively, in another embodiment, for administration by inhalation or insufflation, the compounds of formula I according to the present invention are in the form of a dry powder composition, for example a powder mix of the compound and a suitable powder base such as lactose or starch. In another embodiment, the powder composition is presented in unit dosage form in, for example, capsules or cartridges or e.g. gelatin or blister packs from which the powder may be administered with the aid of an inhalator or insufflator.

In one embodiment, the above described formulations are adapted to give sustained release of the active ingredient.

The compounds of the invention may also be used in combination with other antiviral agents.

In one embodiment, the compounds of the invention may be employed together with at least one other antiviral agent chosen from protease inhibitors, polymerase inhibitors, and helicase inhibitors.

As used in this application, the term "interferon" include: interferon likes molecules such as interferon (IFN), interferon $\alpha$-2a, interferon $\alpha$-2b, consensus interferon (CIFN) and other types of interferons.

In one embodiment, the compounds of the invention may be employed together with at least one other antiviral agent chosen from interferon (IFN), interferon $\alpha$-2a, interferon $\alpha$-2b, consensus interferon (CIFN), ribavirin, amantadine, rimantadine, interleukine-12, ursodeoxycholic acid (UDCA), glycyrrhizin and silyburn marianum.

In one embodiment, the compounds of the invention may be employed together with at least one other antiviral agent chosen from Interferon-$\alpha$, Ribavirin and Amantadine.

In one embodiment, the compounds of the invention may be employed together with at least one other antiviral agent chosen from Interferon-$\alpha$ and Ribavirin (REBETRON).

In one embodiment, the compounds of the invention may be employed together Interferon-α.

In one embodiment, the compounds of the invention may be employed together with Ribavirin.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When the compound (I) or a pharmaceutically acceptable salts thereof is used in combination with a second therapeutic agent active against the same virus the dose of each compound may be either the same as or differ from that when the compound is used alone.

Appropriate doses will be readily appreciated by those skilled in the art.

The following examples are provided to illustrate various embodiments of the present invention and shall not be considered as limiting in scope.

EXAMPLE 1

Preparation of 3'-DEOXYCYTIDINE 5'-TRIPHOSPHATE TRIAMMONIUM SALT
(Compound #2)

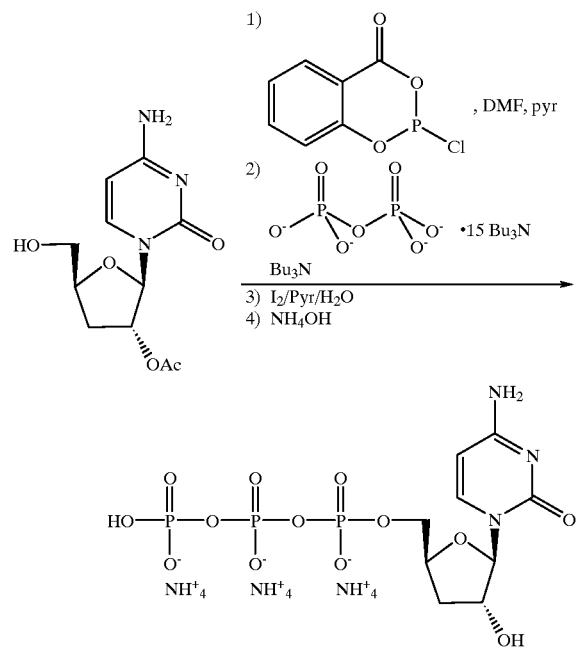

Procedure: To a stirring suspension of 3'-deoxy-2'-acetoxycytidine (15.0 mg, 0.056 mmol) in dry DMF (0.60 ml) was added dry pyridine (0.20 ml) followed by a freshly prepared solution of 2-chloro-4 H-1,3,2-benzodioxaphosphorin-4-one 0.5 M in 1,4-dioxane (111 µl, 0.056 mmol). The mixture was stirred 30 minutes at room temperature, then tributylamine (36 µl, 0.152 mmol) and a solution of tributylammonium pyrophosphate 0.5 M in DMF (101 µl, 0.051 mmol) were added simultaneously. The mixture was stirred another 30 minutes. A solution of I2 1% in pyridine/H2O (98:2) (1.01 ml, 0.081 mmol of I) was added and the mixture was stirred 30 minutes. The excess of iodine was destroyed by adding 0.2 ml of aqueous sodium bisulfite 5%. The mixture was stirred 15 minutes, then it was concentrated under reduced pressure to remove all solvents. The residue was dissolved in water, washed two times with methylene chloride and once with ethyl acetate. The aqueous layer was concentrated and purified by charcoal column as follow: about 400 mg of charcoal, placed over a thin layer of Celite in a funnel with fritted disk, was prewashed by passing methanol, then deionized water (by vaccuum). The crude residue was diluted in a minimum of water, acidified to pH 1–2 by adding few drops of HCl 1N, then placed on the top of the charcoal column. The column was eluted with deionized water (35 ml) in order to remove inorganic salts, then 0.5 N ammonia (15 ml) to collect the desired triphosphate. The collected triphophate was concentrated and diluted in deionized water (1 ml) and concentrated NH4OH (2 ml). The mixture was stirred one hour at room temperature to cleave the acetyl group, then concentrated to dryness. The residue was purified on a pad of C18 RP silica gel eluting with deionized water (the desired triphosphate comes out fast). The fractions containing the desired triphosphate were collected and lyophilized to give the 3'-deoxycytidine 5'-triphosphate triammonium salt as a yellowish solid (18 mg, 69% yield, purity >85% evaluated by 1H and 31P-NMR). 1H NMR (400 MHz, D2O) δ: 7.90 (d, 1 H, 7.5 Hz), 5.99 (d, 1 H, 7.5 Hz), 5.73 (s, 1 H), 4.55 (s, 1 H), 4.35 (d, 1 H, 5.0 Hz), 4.26 (m, 1 H), 4.04 (m, 1 H), 2.05 (m, 1 H), 1.94 (m, 1 H) ppm. 31P NMR (162 MHz, D2O) δ: −5.9 (br.s), −10.4 (d, 19 Hz), −21.5 (br.s) ppm. In a similar manner, the compounds of the invention can be obtained.

EXAMPLE 2

Evaluation of Triphosphate Analogues

In The HCV RNA-Dependent RNA Polymerase Assay- The following references which are referenced in the example are all incorporated by reference:

1. Behrens, S., Tomei, L., De Francesco, R. (1996) *EMBO* 15, 12–22.
2. Harlow, E, and Lane, D. (1988) *Antibodies: A Laboratory Manual*. Cold Spring Harbord Laboratory. Cold Spring Harbord. N.Y.
3. Lohmann, V., Körner, F., Herian, U., and Bartenschlager, R. (1997) *J. Virol.* 71, 8416–8428.

Compounds were evaluated using an in vitro polymerase assay containing purified recombinant HCV RNA-dependent RNA polymerase (NS5B protein). HCV NS5B was expressed in insect cells using a recombinant baculovirus as vector. The experimental procedures used for the cloning, expression and purification of the HCV NS5B protein are described below. Following are details of the RNA-dependent RNA polymerase assays used to test the compounds.

Expression of the HCV NS5B Protein in Insect Cells:

The cDNA encoding the entire NS5B protein of HCV-Bk strain, genotype 1b, was amplified by PCR using a plasmid containing a cDNA version of the full-length HCV genome as template. The oligonucleotides used to amplify this HCV region were designed to introduce a NheI site followed by an ATG at the 5' end of the NS5B coding region as well as a BamHI site at the 3' end immediately downstream of the translation stop codon. The amplified sequence, of 1.8 kb, was digested with NheI and BamHI and ligated to a predigested pBlueBacII plasmid (Invitrogen). The resulting recombinant plasmid was designated pBac/NS5B. Sf9 cells were co-transfected with 3 µg of pBac/NS5B, together with 1 µg of linearized baculovirus DNA (Invitrogen), as described in the manufacturer's protocol. Following two rounds of plaque purification, an NS5B-recombinant baculovirus, BacNS5B, was isolated. The presence of the recombinant NS5B protein was determined by western blot analysis (Harlow and Lane, 1988) of BacNS5B-infected Sf9 cells, using a HCV NS5B specific rabbit polyclonal antiserum (anti-NS5B). Infections of Sf9 cells with this plaque purified virus were performed in one-liter spinner flasks at a cell density of $1.2 \times 10^6$ cells/ml and a multiplicity of infection of 5.

Preparation of a Soluble Recombinant NS5B Protein:

Sf9 cells were infected as described above. Sixty hours post-infection, cells were harvested then washed twice with phosphate buffer saline (PBS). Total proteins were solubilized as described in Lohmann et al. (1989) with some modifications. In brief, proteins were extracted in three steps, S1, S2, S3, using lysis buffers (LB) I, LB II and LB III (Lohmann et al, 1997). The composition of LBII was modified to contain 0.1% triton X-100 and 150 mM NaCl to reduce the amount of solubilized NS5B protein at this step. In addition, sonication of cell extracts was avoided throughout the protocol to preserve the integrity of the protein structure.

Purification of Recombinant NS5B Using Fast Protein Liquid Chromatography (FPLC):

Soluble NS5B protein in the S3 fraction was diluted to lower the NaCl concentration to 300 mM, then it incubated batchwise with DEAE sepharose beads (Amersham-Pharmacia) for 2 hrs at 4° C., as described by Behrens et al. (1989). Unbound material was cleared by centrifugation for 15 min at 4° C., at 25 000 rpm using a SW41 rotor (Beckman). The supernatant was further diluted to lower the NaCl concentration to 200 mM and subsequently loaded, with a flow rate of 1 ml/min, on a 5 ml HiTrap® heparin column (Amersham-Pharmacia) connected to an FPLC® system (Amersham-Pharmacia). Bound proteins were eluted in 1 ml fractions, using a continuous NaCl gradient of 0.2 to 1 M, over a 25 ml volume. NS5B-containing fractions were identified by sodium dodecyl sulfate polyacrylamide gel electrophoresis (SDS-PAGE), followed by western blotting using the anti-NS5B antiserum at a dilution of 1:2000. Positive fractions were pooled and the elution buffer was exchanged against a 50 mM $NaPO_4$ pH 7.0, 20% glycerol, 0.5% triton X-100 and 10 mM DTT, using a PD-10 column (Amersham-Pharmacia). The sample was then loaded onto a 1 ml HiTrap® SP column (Amersham-Pharmacia), with a flow rate of 0.1 ml/min. Bound proteins were eluted using a continuous 0 to 1 M NaCl gradient over a 15 ml volume. Eluted fractions were analyzed by SDS-PAGE and western blotting. Alternatively, proteins were visualized, following SDS-PAGE, by silver staining using the Silver Stain Plus kit (BioRad) as described by the manufacturer. Positive fractions were tested for RdRp activity (see below) and the most active ones were pooled, and stored as a 40% glycerol solution at −70° C.

In vitro RNA-dependent RNA Polymerase Assays Used to Evaluate the Triphosphate Form of Nucleoside Analogues:

RdRp assays were conducted using in vitro transcribed heteropolymeric RNA templates.

RdRp reactions were performed in a total volume of 50 µl of a buffer consisting of 20 mM Tris-HCl pH 7.5, 1 mM DTT, 50 mM NaCl, 0.5 mM $MnCl_2$ and 5 MM $MgCl_2$. Standard HCV RdRp reactions contained 200 ng of purified NS5B protein. The substrate mixture included in the assay depended on the base of the nucleoside triphosphate to be tested (adenine, guanine, cytosine or uracil analogue). The NTP substrate with a similar base to that of the inhibitor, was added at twice the measured Km. This concentration included 5 µCi (3000 Ci/mmol) of a [$^{32}$P] version of this nucleotide. The remaining three substrates were used at 100 µM. The measured Kms for the four substrates were as follows: 18 µM for ATP, 0.5 µM for CTP and GTP, and 1.2 µM for UTP. Following a two hour incubation at 22° C., reactions were stopped by the addition of 100 µg of sonicated salmon sperm DNA (Life Technologies) and 1 ml of 10% trichloroacetic acid (TCA)-0.5% tetrasodium pyrophosphate (PPi). Nucleic acids were precipitated at 4° C. for 30 min after which samples were filtered on GF/C glass microfiber filters (Millipore). Membranes were subsequently washed with 25 ml of a 1% TCA-0.1% PPi solution, then air dried. Incorporated radioactivity was quantified using a liquid scintillation counter (1450-Microbeta, Wallac).

Heteropolymeric RNA templates were generated by run-off transcription. As template for these transcription reactions, a recombinant pcDNA3 plasmid (Invitrogen) containing a cDNA version of the HCV genome was used and referred to as pcDNA/HCVfl. In vitro transcriptions were performed using the MEGAscript™ kit (Ambion), as suggested by the manufacturer. In brief, the plasmid pcDNA/HCVfl was linearized with EcoRI to generate a truncated HCV transcript of about 6900 nucleotides. Linearized DNA was extracted with a one to one volume of phenol/chloroform, precipitated with ethanol, then 1 µg of this linearized DNA was used as template in T7 RNA polymerase-driven in vitro transcription reactions. Transcripts were extracted using the TRIZOL® reagent (Life Technologies) and an aliquot (1 µg) was used as template in RdRp assays.

| Compound | HCV polymerase $IC_{50}$ |
| --- | --- |
| COMPOUND#2 | 0.036 µM |
| COMPOUND#4 | 0.3 µM |
| COMPOUND#6 | 0.26 µM |
| COMPOUND#8 | 1.98 µM |
| COMPOUND#10 | 6.4 µM |
| COMPOUND#12 | 0.048 µM |
| COMPOUND#14 | 3.1 µM |
| COMPOUND#16 | 0.36 µM |
| COMPOUND#18 | 6.88 µM |
| COMPOUND#20 | 0.18 µM |
| COMPOUND#22 | 0.12 µM |
| COMPOUND#24 | 0.055 µM |
| COMPOUND#26 | 0.91 µM |
| COMPOUND#28 | 2.1 µM |
| COMPOUND#30 | 2.9 µM |
| COMPOUND#32 | 6.8 µM |
| COMPOUND#54 | 9.0 µM |

What is claimed is:

1. A method for the treatment of an hepatitis C infection in a host comprising administering to said host a therapeutically effective amount of a compound having the formula Ib or a pharmaceutically acceptable salt thereof:

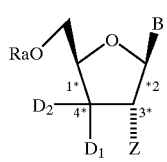

(Ib)

wherein
- B is a nucleotide purine radical, a nucleotide pyrimidine radical or an analogue of a nucleotide purine radical or a nucleotide pyrimidine radical, wherein said analogue is derived by replacement of a CH moiety by a nitrogen atom in a nucleotide purine or pyrimidine radical, replacement of a nitrogen atom by a CH moiety in a nucleotide purine or pyrimidine radical, or both; or derived by removal of ring substituents of said nucleotide purine radical or pyrimidine radical; or combinations thereof; and said analogue is optionally substituted by halogen, hydroxyl, amino, or $C_{1-6}$ alkyl;
- Ra is H, monophosphate, diphosphate, triphosphate, carbonyl which is substituted by a straight, branched or cyclic alkyl having up to 6 C atoms wherein the alkyl is unsubstituted or substituted by halogen, nitro, $CONH_2$, COOH, $O-C_{1-6}$ alkyl, $O-C_{2-6}$ alkenyl, $O-C_{2-6}$ alkynyl, hydroxyl, amino, or COOQ, $C_{2-6}$ alkenyl which is unsubstituted or substituted by halogen, nitro, $CONH_2$, COOH, $O-C_{1-6}$ alkyl, $O-C_{2-6}$ alkenyl, $O-C_{2-6}$ alkynyl, hydroxyl, amino, or COOQ, $C_{2-6}$ alkynyl which is unsubstituted or substituted by halogen, nitro, $CONH_2$, COOH, $O-C_{1-6}$ alkyl, $O-C_{2-6}$, alkenyl, $O-C_{2-6}$ alkynyl, hydroxyl, amino, or COOQ, $C_{6-10}$ aryl which is unsubstituted or mono- or di-substituted with OH, SH, amino, halogen or $C_{1-6}$ alkyl, or

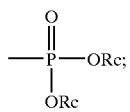

- Rc is, in each case independently, H, straight chain, branched chain or cyclic $C_{1-6}$ alkyl which is unsubstituted or substituted by or substituted by halogen, nitro, $CONH_2$, COOH, $O-C_{1-6}$ alkyl, $O-C_{2-6}$ alkenyl, $O-C_{2-6}$ alkynyl, hydroxyl, amino, or COOQ, $C_{2-6}$ alkenyl which is unsubstituted or substituted by or substituted by halogen, nitro, $CONH_2$, COOH, $O-C_{1-6}$ alkyl, $O-C_{2-6}$ alkenyl, $O-C_{2-6}$ alkynyl, hydroxyl, amino, or COOQ, $C_{2-6}$ alkynyl which is unsubstituted or substituted by or substituted by halogen, nitro, $CONH_2$, COOH, $O-C_{1-6}$ alkyl, $O-C_{2-6}$ alkenyl, $O-C_{2-6}$ alkynyl, hydroxyl, amino, or COOQ, $C_{6-10}$ aryl which is unsubstituted or mono- or di-substituted with OH, SH, amino, halogen or $C_{1-6}$ alkyl, or a hydroxy protecting group;
- Q is $C_{1-6}$ alkyl, $C_{2-6}$ alkenyl, or $C_{2-6}$ alkynyl;
- Z is ORb;
- Rb is H, straight chain, branched chain or cyclic $C_{1-6}$ alkyl which is unsubstituted or substituted by or substituted by halogen, nitro, $CONH_2$, COOH, $O-C_{1-6}$ alkyl, $O-C_{2-6}$ alkenyl, $O-C_{2-6}$ alkynyl, hydroxyl, amino, or COOQ, $C_{2-6}$ alkenyl which is unsubstituted or substituted by or substituted by halogen, nitro, $CONH_2$, COOH, $O-C_{1-6}$ alkyl, $O-C_{2-6}$ alkenyl, $O-C_{2-6}$ alkynyl, hydroxyl, amino, or COOQ, $C_{2-6}$ alkynyl which is unsubstituted or substituted by or substituted by halogen, nitro, $CONH_2$, COOH, $O-C_{1-6}$ alkyl, $O-C_{2-6}$ alkenyl, $O-C_{2-6}$ alkynyl, hydroxyl, amino, or COOQ, $C_{1-6}$ acyl, or a hydroxy protecting group;
- $D_1$ and $D_2$ are each independently $N_3$, F, or H, wherein $D_1$ and $D_2$ are not both H; or
- $D_1$ and $D_2$ together form $=CH_2$, $=CF_2$, or $C_3$-cycloalkyl which is unsubstituted or substituted by halogen, nitro, $CONH_2$, COOH, $O-C_{1-6}$ alkyl, $O-C_{2-6}$ alkenyl, $O-C_{2-6}$ alkynyl, hydroxyl, amino, or COOQ.

2. A method according to claim 1, wherein Z is OH.

3. A method according to claim 2 wherein $D_1$ is H and $D_2$ is F.

4. A method according to claim 2, wherein Ra is H, monophosphate, diphosphate, or triphosphate.

5. A method according to claim 2 wherein Ra is triphosphate.

6. A method according to claim 2 wherein Ra is H.

7. A method according to claim 3, wherein Ra is H, monophosphate, diphosphate, or triphosphate.

8. A method according to claim 3 wherein Ra is triphosphate.

9. A method according to claim 3 wherein Ra is H.

10. A method according to claim 2, wherein B is adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, uracil-1 -yl, 3-carboxamido-1,2,4-triazol-1-yl, 3-deaza-adenin-9-yl, 3-deaza-guanin-9-yl, 3-deaza-inosin-9-yl, 3-deaza-2-amino-purin-9-yl, 3-deaza-2-amino-6-chloro-purin-9-yl 3-deaza-2-6-diamino-purin-9-yl, 7-deaza-adenin-9-yl, 7-deaza-guanin-9-yl, 7-deaza-inosin-9-yl, 7-deaza-2-amino-purin-9-yl, 7-deaza-2-amino-6-chloro-purin-9-yl, 7-deaza-2-6-diamino-purin-9-yl, 7-deaza-8-aza-adenin-9-yl, 7-deaza-8-aza-guanin-9-yl, 7-deaza-8-aza-inosin-9-yl, 7-deaza-8-aza-2-amino-purin-9-yl, 7-deaza-8-aza-2-amino-6-chloro-purin-9-yl, 7-deaza-8-aza-2-6-diamino-purin-9-yl, 8-aza-adenin-9-yl, 8-aza-guanin-9-yl, 8-aza-inosin-9-yl, 8-aza-2-amino-purin-9-yl, 8-aza-2-amino-6-chloro-purin-9-yl, 8-aza-2-6-diamino-purin-9-yl, 5-aza-thymin-1-yl, 5-aza-cytosin-1-yl, 5-aza-uracil-1yl, 6-aza-thymin-1-yl, 6-aza-cytosin-1-yl, or 6-aza-uracil-1-yl;
   which in each case is unsubstituted or substituted by at least one of $NHR_3$, $C_{1-6}$alkyl, $-OC_{1-6}$alkyl, Br, Cl, F, I or OH, wherein $R_3$ is H, $C_{1-6}$alkyl or $C_{1-6}$acyl.

11. A method according to claim 3, wherein B is adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, uracil-1-yl, 3-carboxamido-1,2,4-triazol-1-yl, 3-deaza-adenin-9-yl, 3-deaza-guanin-9-yl, 3-deaza-inosin-9-yl, 3-deaza-2-amino-purin-9-yl, 3-deaza-2-amino-6-chloro-purin-9-yl 3-deaza-2-6-diamino-purin-9-yl, 7-deaza-adenin-9-yl, 7-deaza-guanin-9-yl, 7-deaza-inosin-9-yl, 7-deaza-2-amino-purin-9-yl, 7-deaza-2-amino-6-chloro-purin-9-yl, 7-deaza-2-6-diamino-purin-9-yl, 7-deaza-8-aza-adenin-9-yl, 7-deaza-8-aza-guanin-9-yl, 7-deaza-8-aza-inosin-9-yl, 7-deaza-8-aza-2-amino-purin-9-yl, 7-deaza-8-aza-2-amino-6-chloro-purin-9-yl, 7-deaza-8-aza-2-6-diamino-purin-9-yl, 8-aza-adenin-9-yl, 8-aza-guanin-9-yl, 8-aza-inosin-9-yl, 8-aza-2-amino-purin-9-yl, 8-aza-2-amino-6-chloro-purin-9-yl, 8-aza-2-6-diamino-purin-9-yl, 5-aza-thymin-1-yl, 5-aza-cytosin-1-yl, 5-aza-uracil-1-yl, 6-aza-thymin-1-yl, 6-aza-cytosin-1-yl, or 6-aza-uracil-1-yl;
   which in each case is unsubstituted or substituted by at least one of $NHR_3$, $C_{1-6}$alkyl, $-OC_{1-6}$alkyl, Br, Cl, F, I or OH, wherein $R_3$ is H, $C_{1-6}$alkyl or $C_{1-6}$acyl.

12. A method according to claim 2, wherein B is adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, 5-fluoro-cytosin-1-yl, uracil-1-yl, 5-fluorouracil or 1,2,4-triazole-3-carboxamide base.

13. A method according to claim 3, wherein B is adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, 5-fluoro-cytosin-1-yl, uracil-1-yl, 5-fluorouracil or 1,2,4-triazole-3-carboxamide base.

14. A method according to claim 1, wherein the compound is:
  3'-fluoro-3'-deoxyguanosine or a pharmaceutically acceptable salt thereof;
  3'-fluoro-3'-deoxyguanosine -5'triphosphate or a pharmaceutically acceptable salt thereof;
  3'-fluoro 3'-deoxycytidine or a pharmaceutically acceptable salt thereof;
  3'-fluoro 3'-deoxycytidine-5'triphosphate or a pharmaceutically acceptable salt thereof;
  3'-spirocyclopropyl-3'-deoxyguanosine or a pharmaceutically acceptable salt thereof;
  3'-spirocyclopropyl-3'-deoxyguanosine-5'triphosphate or a pharmaceutically acceptable salt thereof;
  3'-difluoro-spirocyclopropyl-3'-deoxyguanosine or a pharmaceutically acceptable salt thereof;
  3'-difluoro-spirocyclopropyl-3'-deoxyguanosine-5'triphosphate or a pharmaceutically acceptable salt thereof;
  3'-methylene-3'-deoxyguanosine or a pharmaceutically acceptable salt thereof;
  3'-methylene-3'-deoxyguanosine-5'triphosphate or a pharmaceutically acceptable salt thereof;
  3'-difluromethylene 3'-deoxyguanosine or a pharmaceutically acceptable salt thereof;
  3'-difluromethylene 3'-deoxyguanosine-5'triphosphate or a pharmaceutically acceptable salt thereof;
  3'-spirocyclopropyl-3'-deoxycytidine or a pharmaceutically acceptable salt thereof;
  3'-spirocyclopropyl-3'-deoxycytidine-5'triphosphate or a pharmaceutically acceptable salt thereof;
  3'-difluoro-spirocyclopropyl-3'-deoxycytidine or a pharmaceutically acceptable salt thereof;
  3'-difluoro-spirocyclopropyl-3'-deoxycytidine-5'triphosphate or a pharmaceutically acceptable salt thereof;
  3'-methylene-3'-deoxycytidine or a pharmaceutically acceptable salt thereof;
  3'-methylene-3'-deoxycytidine -5'triphosphate or a pharmaceutically acceptable salt thereof;
  3'-difluromethylene 3'-deoxycytidine or a pharmaceutically acceptable salt thereof;
  3'-difluromethylene 3'-deoxycytidine-5'triphosphate or a pharmaceutically acceptable salt thereof;
  3'-azido-3'-deoxycytidine or a pharmaceutically acceptable salt thereof; or
  3'-azido-3'-deoxycytidine 5'triphosphate or a pharmaceutically acceptable salt thereof.

15. A method according to claim 1, further comprising administering at least one further therapeutic agent chosen from interferon, interferon α-2a, interferon α-2b, consensus interferon, ribavirin, amantadine, rimantadine, interleukine-12, ursodeoxycholic acid, glycyrrhizin and silyburn marianum.

16. A method according to claim 2, further comprising administering at least one further therapeutic agent chosen from interferon, interferon α-2a, interferon α-2b, consensus interferon, ribavirin, amantadine, rimantadine, interleukine-12, ursodeoxycholic acid, glycyrrhizin and silyburn marianum.

17. A method according to claim 3, further comprising administering at least one further therapeutic agent chosen from interferon, interferon α-2a, interferon α-2b, consensus interferon, ribavirin, amantadine, rimantadine, interleukine-12, ursodeoxycholic acid, glycyrrhizin and silyburn marianum.

18. A method according to claim 14, further comprising administering at least one further therapeutic agent chosen from interferon, interferon α-2a, interferon α-2b, consensus interferon, ribavirin, amantadine, rimantadine, interleukine-12, ursodeoxycholic acid, glycyrrhizin and silyburn marianum.

19. A method according to claim 1, wherein
  Ra is H, monophosphate, diphosphate, triphosphate, carbonyl substituted by $C_{1-6}$ alkyl, $C_{2-6}$ alkenyl, $C_{2-6}$ alkynyl, or $C_{6-10}$ aryl or

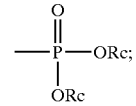

Rc is, in each case independently, H, $C_{1-6}$ alkyl, $C_{2-6}$ alkenyl, $C_{2-6}$ alkynyl, $C_{6-10}$ aryl or a hydroxy protecting group selected from acetyl-2-thioethyl ester, pivaloyloxymethyl ester and isopropyloxycarbonyloxymethyl ester; and
  Rb is H, $C_{1-6}$ alkyl, $C_{2-6}$ alkenyl, $C_{2-6}$ alkynyl, $C_{1-6}$ acyl, or a hydroxy protecting group selected from acetyl-2-thioethyl ester, pivaloyloxymethyl ester and isopropyloxycarbonyloxymethyl ester.

20. A method according to claim 1, wherein B is adenin-9-yl, guanin-9-yl, inosin-9-yl, 2-amino-purin-9-yl, 2-amino-6-chloro-purin-9-yl, 2-6-diamino-purin-9-yl, thymin-1-yl, cytosin-1-yl, uracil-1-yl, or 3-carboxamido-1,2,4-triazol-1-yl, which in each case is unsubstituted or substituted by at least one of $NHR_3$, $C_{1-6}$alkyl, $-OC_{1-6}$alkyl, Br, Cl, F, I or OH, wherein $R_3$ is H, $C_{1-6}$alkyl or $C_{1-6}$acyl.

21. A method according to claim 1, wherein B is adenin-9-yl, guanin-9-yl, 2-amino-purin-9-yl, 2-amino-6-chloro-purin-9-yl, 2-6-diamino-purin-9-yl, thymin-1-yl, cytosin-1-yl, uracil-1-yl, which in each case is unsubstituted or substituted by at least one of $NHR_3$, $C_{16}$alkyl, $-OC_{1-6}$alkyl, Br, Cl, F, I or OH, wherein $R_3$ is H, $C_{1-6}$alkyl or $C_{1-6}$acyl.

22. A method according to claim 1, wherein B is guanin-9-yl, cytosin-1-yl, uracil-1-yl, which in each case is unsubstituted or substituted by at least one of $NHR_3$, $C_{1-6}$alkyl, $-OC_{1-6}$alkyl, Br, Cl, F, I or OH, wherein $R_3$ is H, $C_{1-6}$alkyl or $C_{1-6}$acyl.

23. A method according to claim 1, wherein B is guanin-9-yl, cytosin-1-yl, 5'-fluoro-cytosin-1-yl, 5'-fluorouracil-1-yl or uracil-1-yl.

24. A method according to claim 1, wherein B is

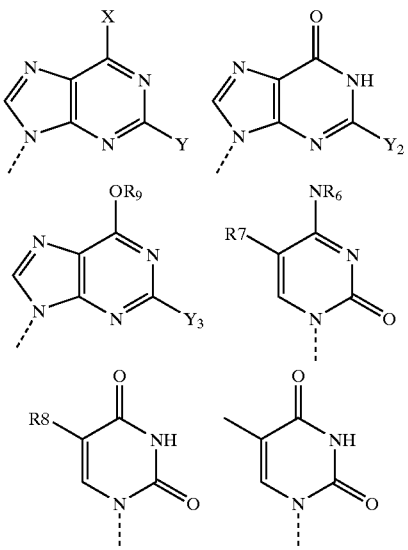

wherein
- X is H, halogen or $NHR_{10}$;
- $R_{10}$ is H, $C_{1-6}$acyl, $C_{1-6}$ alkyl, $C_{2-6}$ alkenyl, or $C_{2-6}$ alkynyl;
- Y is H, halogen or $NHR_{11}$;
- $R_{11}$ is H, $C_{1-6}$acyl, $C_{1-6}$ alkyl, $C_{2-6}$ alkenyl, or $C_{2-6}$ alkynyl;
- $Y_2$ is H, halogen or $NHR_{12}$;
- $R_{12}$ is H, $C_{1-6}$acyl, $C_{1-6}$ alkyl, $C_{2-6}$ alkenyl, or $C_{2-6}$ alkynyl;
- $R_9$ is H, hydroxy protecting group, $C_{1-6}$acyl, $C_{1-6}$ alkyl, $C_{2-6}$ alkenyl, or $C_{2-6}$ alkynyl;
- $Y_3$ is H, halogen or $NHR_{13}$;
- $R_{13}$ is H, $C_{1-6}$acyl, $C_{1-6}$ alkyl, $C_{2-6}$ alkenyl, or $C_{2-6}$ alkynyl;
- $R_7$ is H, halogen, $C_{1-6}$acyl, $C_{1-6}$ alkyl, $C_{2-6}$ alkenyl, or $C_{2-6}$ alkynyl; and
- $R_8$ is H, halogen, $C_{1-6}$acyl, $C_{1-6}$ alkyl, $C_{2-6}$ alkenyl, or $C_{2-6}$ alkynyl.

25. A method according to claim 24, wherein X is H, F, or $NHR_{10}$, $R_{10}$ is H, Y is H, F, or $NHR_{11}$, $R_{11}$ is H, $Y_2$ is H, F, or $NHR_{12}$, $R_{12}$ is H, $R_9$ is H, $Y_3$ is H, F, or $NHR_{13}$, $R_{13}$ is H, $R_7$ is H, F, or $C_{1-6}$ alkyl, and $R_8$ is H, F, or $C_{1-6}$ alkyl.

26. A method according to claim 1, wherein Z is F or ORb, and Rb is H or methyl.

27. A method according to claim 1, wherein $D_1$ and $D_2$ are $N_3$, F, or H in which $D_1$ and $D_2$ are not both H, or $D_1$ and $D_2$ together form cyclopropyl, difluorocyclopropyl —=$CH_2$, or —=$CF_2$.

28. A method according to claim 1, wherein said compound is administered in an amount of 0.01 to about 750 mg/kg of body weight per day.

29. A method according to claim 1, wherein said compound is administered in unit dosages containing 10 to 1500 mg of said compound per unit dosage.

30. A method according to claim 15, wherein said compound and said further therapeutic agent are each administered as a formulation which further contains a pharmaceutically acceptable carrier.

31. A method according to claim 30, wherein said compound and said further therapeutic agent are sequentially administered, in separate or combined pharmaceutical formulations.

32. A method according to claim 30, wherein said compound and said further therapeutic agent are simultaneously administered, in separate or combined pharmaceutical formulations.

33. A method according to claim 1, wherein said host is a human.

34. A method according to claim 2, wherein said host is a human.

35. A method according to claim 3, wherein said host is a human.

36. A method according to claim 14, wherein said host is a human.

37. A method for the treatment of an hepatitis C infection in a host comprising administering a therapeutically effective amount of a compound having the formula Ib or a pharmaceutically acceptable salt thereof:

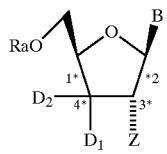

(Ib)

wherein
- B is a nucleotide purine radical, a nucleotide pyrimidine radical or an analogue of a nucleotide purine radical or a nucleotide pyrimidine radical, wherein said analogue is derived by replacement of a CH moiety by a nitrogen atom in a nucleotide purine or pyrimidine radical, replacement of a nitrogen atom by a CH moiety in a nucleotide purine or pyrimidine radical, or both; or derived by removal of ring substituents of said nucleotide purine radical or pyrimidine radical; or combinations thereof; and said analogue is optionally substituted by halogen, hydroxyl, amino, or $C_{1-6}$alkyl;
- Ra is H, monophosphate, diphosphate, triphosphate, carbonyl which is substituted by a straight, branched or cyclic alkyl having up to 6 C atoms wherein the alkyl is unsubstituted or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ, $C_{2-6}$ alkenyl which is unsubstituted or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ, $C_{2-6}$ alkynyl which is unsubstituted or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ, $C_{6-10}$ aryl which is unsubstituted or mono- or di-substituted with OH, SH, amino, halogen or $C_{1-6}$ alkyl, or

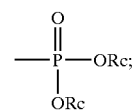

- Rc is, in each case independently, H, straight chain, branched chain or cyclic $C_{1-6}$ alkyl which is unsubstituted or substituted by or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ, $C_{2-6}$ alkenyl which is unsubstituted or substituted by or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ, $C_{2-6}$ alkynyl which is unsubstituted or substituted by or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ, $C_{6-10}$ aryl which is unsubstituted or mono- or di-substituted with OH, SH, amino, halogen or $C_{1-6}$ alkyl, or a hydroxy projecting group;

Q is $C_{1-6}$ alkyl, $C_{2-6}$ alkenyl, or $C_{2-6}$ alkynyl;

Z is ORb;

Rb is H, straight chain, branched chain or cyclic $C_{1-6}$ alkyl which is unsubstituted or substituted by or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ, $C_{2-6}$ alkenyl which is unsubstituted or substituted by or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ, $C_{2-6}$ alkynyl which is unsubstituted or substituted by or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ, $C_{1-6}$ acyl, or a hydroxy protecting group;

$D_1$ and $D_2$ are each independently $N_3$, F or H, wherein $D_1$ and $D_2$ are not both H; or $D_1$ and $D_2$ together form =$CH_2$, =$CF_2$, or $C_3$-cycloalkyl which is unsubstituted or substituted by or substituted by halogen, nitro, $CONH_2$, COOH, O—$C_{1-6}$ alkyl, O—$C_{2-6}$ alkenyl, O—$C_{2-6}$ alkynyl, hydroxyl, amino, or COOQ;

with the proviso that:

said method does not include administration of an interferon.

38. A method according to claim 37, wherein said host is a human.

* * * * *

UNITED STATES PATENT AND TRADEMARK OFFICE
CERTIFICATE OF CORRECTION

PATENT NO.       : 6,784,161 B2
APPLICATION NO.  : 09/785235
DATED            : August 31, 2004
INVENTOR(S)      : Ismaili et al.

It is certified that error appears in the above-identified patent and that said Letters Patent is hereby corrected as shown below:

Column 28, line 64, reads "of an hepatitis" should read -- of a hepatitis --
Column 29, line 34, reads "O—$C_{2-6}$," should read -- O-$C_{2-6}$ --
Column 29, line 46, reads "or substituted by or substituted by" should read
       -- or substituted by --
Column 29, line 49, reads "unsubstituted or substituted by or" should read
       -- unsubstituted or --
Column 29, line 53, reads "unsubstituted or substituted by or substituted by or" should
       read -- unsubstituted or --
Column 29, line 64, reads "unsubstituted or substituted by or" should read
       -- unsubstituted or --
Column 30, line 1, reads "by or substituted by halogen," should read -- by halogen, --
Column 30, line 4, reads "unsubstituted or substituted by or" should read
       -- unsubstituted or --
Column 32, line 32, reads "chloro-purin-9-yl" should read -- chloro-purin-9-yl, --
Column 30, line 42, reads "5-aza-uracil-1yl," should read -- 5-aza-uracil-1-yl, --
Column 30, line 53, reads "chloro-purin-9-yl" should read -- chloro-purin-9-yl, --
Column 31, line 19, reads "3'-fluoro 3'-" should read -- 3'-fluoro-3' --
Column 31, line 21, reads "3'-fluoro 3'-" should read -- 3'-fluoro-3' --
Column 31, line 38, reads "3'difluromethylene 3'-" should read
       -- 3'-difluoromethylene-3' --
Column 31, line 40, reads "3'difluromethylene 3'-" should read
       -- 3'-difluoromethylene-3' --
Column 31, line 57, reads "3'difluromethylene 3'-" should read
       -- 3'-difluoromethylene-3' --
Column 31, line 59, reads "3'difluromethylene 3'-" should read
       -- 3'-difluoromethylene-3' --
Column 31, line 64, reads "deoxycytidine 5'triphosphate" should read
       -- deoxycytidine-5'triphosphate --
Column 32, line 3, reads "silyburn" should read -- silybum --
Column 32, line 10, reads "silyburn" should read -- silybum --
Column 32, line 16, reads "silyburn" should read -- silybum --
Column 32, line 23, reads "silyburn" should read -- silybum --

UNITED STATES PATENT AND TRADEMARK OFFICE
CERTIFICATE OF CORRECTION

PATENT NO. : 6,784,161 B2
APPLICATION NO. : 09/785235
DATED : August 31, 2004
INVENTOR(S) : Ismaili et al.

It is certified that error appears in the above-identified patent and that said Letters Patent is hereby corrected as shown below:

Column 32, line 57, reads "$C_{16}$" should read -- $C_{1-16}$ --
Column 33, line 11, reads "R7" should read – $R_7$ --
Column 33, line 19, reads "R8" should read -- $R_8$ --
Column 33, line 19, insert -- or -- between last two formulas
Column 33, line 52, reads "difluorocyclopropyl" should read -- difluorocyclopropyl, --

Signed and Sealed this

Seventeenth Day of November, 2009

David J. Kappos
*Director of the United States Patent and Trademark Office*